US009464270B2

(12) United States Patent
Kakulas

(10) Patent No.: US 9,464,270 B2
(45) Date of Patent: Oct. 11, 2016

(54) STEM CELL PREPARATIONS AND METHODS OF USE

(71) Applicant: Foteini Kakulas, Western Australia (AU)

(72) Inventor: Foteini Kakulas, Western Australia (AU)

(73) Assignee: Medela Holding AG, Baar (CH)

( * ) Notice: Subject to any disclaimer, the term of this patent is extended or adjusted under 35 U.S.C. 154(b) by 90 days.

(21) Appl. No.: 13/866,221

(22) Filed: Apr. 19, 2013

(65) Prior Publication Data
US 2014/0086882 A1    Mar. 27, 2014

Related U.S. Application Data

(60) Provisional application No. 61/636,081, filed on Apr. 20, 2012.

(51) Int. Cl.
*C12N 5/071* (2010.01)
*C12N 5/0775* (2010.01)

(52) U.S. Cl.
CPC ........... *C12N 5/0602* (2013.01); *C12N 5/0668* (2013.01)

(58) Field of Classification Search
None
See application file for complete search history.

(56) References Cited

U.S. PATENT DOCUMENTS

| 7,776,586 B2 | 8/2010 | Cregan et al. |
| 2007/0059822 A1 | 3/2007 | Cregan et al. |
| 2011/0189136 A1 | 8/2011 | Ratajczak et al. |

FOREIGN PATENT DOCUMENTS

| CN | 101993852 A | 3/2011 |
| WO | 2005/061696 A1 | 7/2005 |

OTHER PUBLICATIONS

Levenstein et al., Basic Fibroblast Growth Factor Support of Human Embryonic Stem Cell Self-Renewal, STEMCELLS, 2006; 24:568-574.*
Asselin-Labat et al., Letters: Control of mammary stem cell function by steroid hormone signalling, Nature. Jun. 10, 2010;465(7299):798-802.
Aubry et al., Striatal progenitors derived from human ES cells mature into DARPP32 neurons in vitro and in quinolinic acid-lesioned rats, PNAS 2008 vol. 105 No. 43, 16707-16712.
Bar-Nur et al., Brief Report: Epigenetic Memory and Preferential Lineage-Specific Differentiation in Induced Pluripotent Stem Cells Derived from Human Pancreatic Islet Beta Cells, Cell Stem Cell. Jul. 8, 2011;9(1):17-23.
Beltran et al., Generation of tumor-initiating cells by exogenous delivery of OCT4 transcription factor, Breast Cancer Research 2011, 13:R94.
Björklund et al., Embryonic stem cells develop into functional dopaminergic neurons after transplantation in a Parkinson rat model, PNAS 2002 vol. 99 No. 4, 2344-2349.
Bjornson et al., Reports: Turning Brain into Blood: A Hematopoietic Fate Adopted by Adult Neural Stem Cells in Vivo, Science. Jan. 22, 1999;283(5401):534-7.
Clarke et al., Reports: Generalized Potential of Adult Neural Stem Cells, Science. Jun. 2, 2000;288(5471):1660-3.
Cregan et al., Identification of nestin-positive putative mammary stem cells in human breastmilk, Cell Tissue Res. Jul. 2007;329(1):129-36.
Ding et al., Oct4 links multiple epigenetic pathways to the pluripotency network, Cell Research (2012) 22:155-167.
Dontu et al., In vitro propagation and transcriptional profiling of human mammary stem/progenitor cells, Genes Dev. 2003 17: 1253-1270.
Erdö et al., Rapid Communication: Host-Dependent Tumorigenesis of Embryonic Stem Cell Transplantation in Experimental Stroke, Journal of Cerebral Blood Flow & Metabolism 23:780-785.
Evans and Kaufman, Establishment in culture of pluripotential cells from mouse embryos, Nature. Jul. 9, 1981;292(5819):154-6.
Ghosh et al., Dissecting the Oncogenic Potential of Human Embryonic and Induced Pluripotent Stem Cell Derivatives, Cancer Res. 2011 71(14): 5030-5039.
Hedlund et al., Selection of Embryonic Stem Cell-Derived Enhanced Green Fluorescent Protein-Positive Dopamine Neurons Using the Tyrosine Hydroxylase Promoter Is Confounded by Reporter Gene Expression in Immature Cell Populations, Stem Cells. May 2007 ; 25(5): 1126-1135.
Hochedlinger and Plath, Epigenetic reprogramming and induced pluripotency, Development 2009 136, 509-523.
Hoffman, The potential of nestin-expressing hair follicle stem cells in regenerative medicine, Expert Opin Biol Ther. Mar. 2007;7(3):289-91.
Itskovitz-Eldor et al., Differentiation of Human Embryonic Stem Cells into Embryoid Bodies Comprising the Three Embryonic Germ Layers, Molecular Medicine 6(2): 88-95, 2000.
Jiang et al., Pluripotency of mesenchymal stem cells derived from adult marrow, Nature. Jul. 4, 2002;418(6893):41-9.
Joshi et al., Progesterone induces adult mammary stem cell expansion, Nature. Jun. 10, 2010;465(7299):798-802.
Krause et al., Multi-Organ, Multi-Lineage Engraftment by a Single Bone Marrow-Derived Stem Cell, Cell, vol. 105, 369-377.
Lee et al., Three-dimensional culture models of normal and malignant breast epithelial cells, Nat Methods. Apr. 2007 ; 4(4): 359-365.
Lensch et al., Teratoma Formation Assays with Human Embryonic Stem Cells: A Rationale for One Type of Human-Animal Chimera, Cell Stem Cell 2007, 1, 253-258.
Lister et al., Prenatal protein malnutrition alters the proportion but not numbers of parvalbumin-immunoreactive interneurons in the hippocampus of the adult Sprague-Dawley rat, Nutr Neurosci. 2011 14(4): 165-178.
Maherali et al., Directly Reprogrammed Fibroblasts Show Global Epigenetic Remodeling and Widespread Tissue Contribution, Cell Stem Cell 2007 1, 55-70.

(Continued)

*Primary Examiner* — Karen Cochrane Carlson
*Assistant Examiner* — Jennifer M. H. Tichy
(74) *Attorney, Agent, or Firm* — McDonnell Boehnen Hulbert & Berghoff LLP

(57) ABSTRACT

The present invention relates to a method of preparing cells and in particular to a method of preparing breastmilk stem cells (BSCs) by isolation from breastmilk and subsequent culture. The invention further relates to BSCs prepared by the methods of the invention and to methods and uses thereof. The invention has been developed primarily as a method for preparing and culturing BSC.

21 Claims, 18 Drawing Sheets

(56) References Cited

OTHER PUBLICATIONS

Miura et al., Variation in the safety of induced pluripotent stem cell lines, Nat Biotechnol. Aug. 2009;27(8):743-5. doi: 10.1038/nbt.1554.
Molenaar et al., Expression of alpha-lactalbumin, alpha-S1-casein, and lactoferrin genes is heterogeneous in sheep and cattle mammary tissue, J Histochem Cytochem 1992 40: 611.
Ohi et al., Incomplete DNA methylation underlies a transcriptional memory of the somatic cell in human iPS cells, Nat Cell Biol. 2011 13(5): 541-549.
Okita et al., Generation of germline-competent induced pluripotent stem cells, Nature. Jul. 19, 2007;448(7151):313-7.
Pang and Hartmann, Initiation of Human Lactation: Secretory Differentiation and Secretory Activation, J Mammary Gland Biol Neoplasia. Dec. 2007;12(4):211-21.
Pasi et al., Genomic instability in induced stem cells, Cell Death and Differentiation 2011 18, 745-753.
Pruszak et al., Markers and Methods for Cell Sorting of Human Embryonic Stem Cell-Derived Neural Cell Populations, Stem Cells. Sep. 2007 ; 25(9): 2257-2268.
Ratajczak et al., Review: The role of pluripotent embryonic-like stem cells residing in adult tissues in regeneration and longevity, Differentiation. Mar. 2011;81(3):153-61.
Riess et al., Embryonic Stem Cell Transplantation after Experimental Traumatic Brain Injury Dramatically Improves Neurological Outcome, But May Cause Tumors, J Neurotrauma. Jan. 2007;24(1):216-25.
Roy et al., Functional engraftment of human ES cell—derived dopaminergic neurons enriched by coculture with telomerase-immortalized midbrain astrocytes, Nat Med. Nov. 2006;12(11):1259-68.
Shackleton et al., Generation of a functional mammary gland from a single stem cell, Nature. Jan. 5, 2006;439(7072):84-8.
Takahashi and Yamanaka, Induction of Pluripotent Stem Cells from Mouse Embryonic and Adult Fibroblast Cultures by Defined Factors, Cell. Aug. 25, 2006;126(4):663-76.
Takahashi et al., Induction of Pluripotent Stem Cells from Adult Human Fibroblasts by Defined Factors, Cell 131, 861-872.
Taylor-Papadimitriou et al., Growth Requirements Of Human Mammary Epithelial Cells In Culture, Int J Cancer. Dec. 15, 1977;20(6):903-8.
Thomas et al., 14-3-3σ (sigma) regulates proliferation and differentiation of multipotent p63-positive cells isolated from human breastmilk, Cell Cycle 10:2, 278-284.
Thomas et al., Reactive oxygen species initiate luminal but not basal cell death in cultured human mammary alveolar structures: a potential regulator of involution, Cell Death and Disease (2011) 2, e189.
Villadsen et al., Evidence for a stem cell hierarchy in the adult human breast, The Journal of Cell Biology, vol. 177, No. 1, Apr. 9, 2007, 87-101.
Visvader, Keeping abreast of the mammary epithelial hierarchy and breast tumorigenesis, Genes & Development 23:2563-2577.
Wang et al., Increasing CD44+/CD24− tumor stem cells, and upregulation of COX-2 and HDAC6, as major functions of HER2 in breast tumorigenesis, Molecular Cancer 2010, 9:288.
Wernig et al., In vitro reprogramming of fibroblasts into a pluripotent ES-cell-like state, Nature. Jul. 19, 2007;448(7151):318-24.
Wernig et al., A drug-inducible transgenic system for direct reprogramming of multiple somatic cell types, Nat Biotechnol. Aug. 2008 ; 26(8): 916-924.
Young, Control of Embryonic Stem Cell State, Cell. Mar. 18, 2011; 144(6): 940-954.
Yu et al., Induced Pluripotent Stem Cell Lines Derived from Human Somatic Cells, Science. Dec. 21, 2007;318(5858):1917-20.
Fan et al., Unravelling the mystery of stem/progenitor cells in human breast milk, PLOS ONE 2010, vol. 5, No. 12, e14421, 2010.
Hassiotou et al., Stem Cells: Breastmilk contains primitive stem cells from the lactating breast with multi-lineage differentiation potential, FASEB Journal, vol. 26, 913.3, Apr. 2012.
Patki et al., Human breast milk is a rich source of multipotent mesenchymal stem cells, Human Cell, vol. 23, No. 2, 35-40, May 2010.
Fan Y., The Search for Stem Cells in Human Breast Milk. A Thesis Submitted for the Degree of Doctor of Philosophy, Department of Obstetrics and Gynaecology, Yong Loo Lin School of Medicine, National University of Singapore.
Thomas, E., et al., "Reactive Oxygen Species Initiate Luminal But Not Basal Cell Death in Cultured Human Mammary Alveolar Structures: A Potential Regulator of Involution. Cell Death and Disease," 2011, Cell Death and Disease 2: e189.

\* cited by examiner

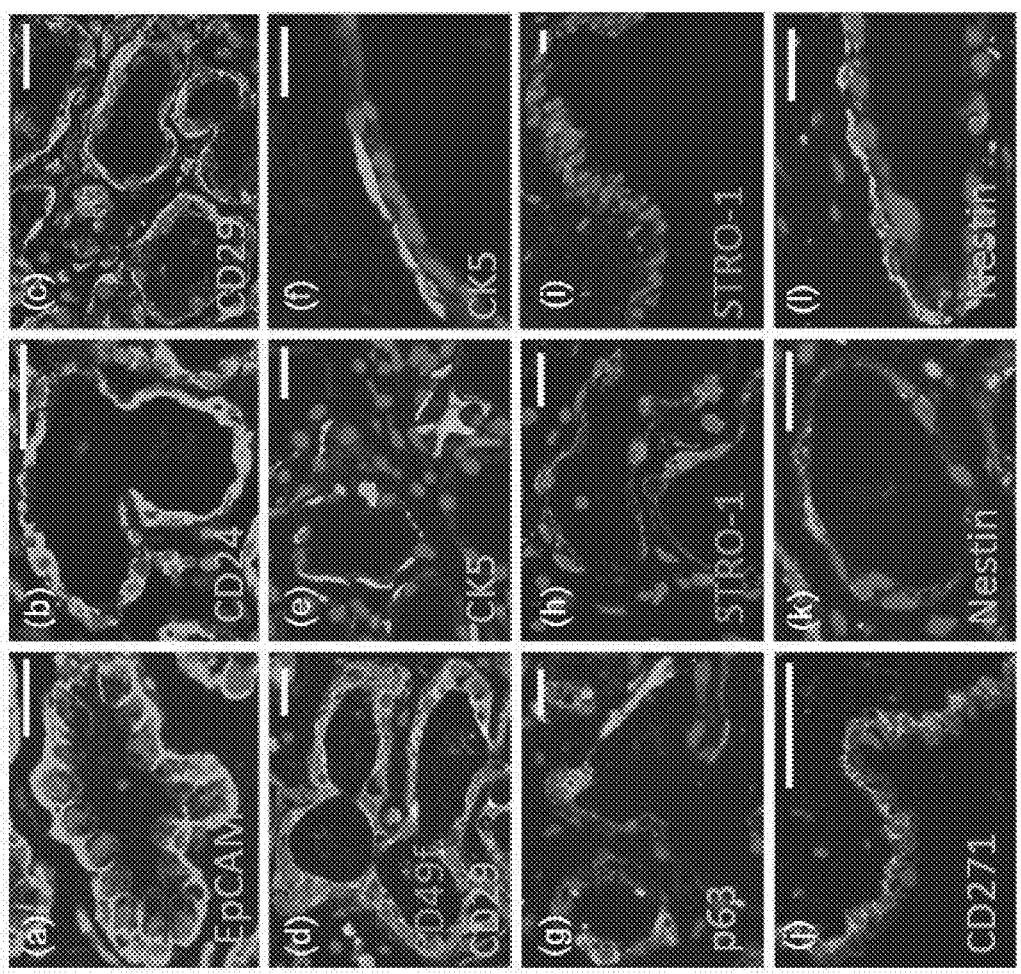

STEM CELL PREPARATIONS AND METHODS OF USE

This application claims the benefit of U.S. Provisional Application Ser. No. 61/636,081, filed Apr. 20, 2012, the disclosure of which is incorporated by reference herein.

FIELD OF THE INVENTION

The present invention relates to a method of preparing cells and in particular to a method of preparing breastmilk stem cells (BSCs) by isolation from breastmilk and subsequent culture. The invention further relates to BSCs prepared by the methods of the invention and to methods and uses thereof. The invention has been developed primarily as a method for preparing and culturing BSCs and will be described hereinafter with reference to this application. However, it will be appreciated that the invention is not limited to this particular field of use.

BACKGROUND

Any discussion of the background art throughout the specification should in no way be considered as an admission that such art is widely known or forms part of common general knowledge in the field.

Stem cells derived from the inner mass of mammalian blastocysts (embryonic stem cells, ESCs) have the ability to self-renew and differentiate into all body cell types (Evans and Kaufman, 1981). These properties have led to expectations that human embryonic stem cells (hESCs) might be useful to treat patients with various diseases and injuries, thereby revolutionizing regenerative medicine.

Cell transplantation therapy using stem cells may offer a viable treatment strategy for patients with disease or injury by (a) providing new cells to replace those lost through disease or injury, or (b) by replacing malfunctioning cells. However, the clinical application of hESCs faces difficulties regarding ethical concerns relating to the use of embryos, as well as instances of tissue rejection after implantation due to immunological incompatibility between patient and donor cells.

One way to circumvent these issues is to artificially derive an embryonic stem cell-like (pluripotent) cell from a mature somatic cell by inducing a "forced" expression of certain genes. These artificially derived embryonic stem cell-like cells are known as induced pluripotent stem (iPS) cells and are believed to be very similar to embryonic stem cells in many respects (Hochedlinger and Plath, 2009). The generation of iPS cells from mature somatic cells, such as fibroblast cells obtained directly from the patient, prevents therapeutic concerns regarding ethics, and may potentially provide the optimal cell source for regenerative medicine. Although immune rejection of autologous iPS cells (i.e. iPS cells derived from the patient) was not considered problematic, recent work suggests that immune rejection of autologous iPS cells may occur (Lister et al., 2011). At the same time, the tumorigenic properties of iPS cells (Ghosh et al., 2011) may prohibit their usage in clinical applications. Moreover, more recent work indicates that iPS cells appear to retain a memory of their somatic program (Ohi et al., 2011) and are characterised by genomic instability (Bar-Nur et al., 2011; Pasi et al., 2011)—another hurdle for the clinical application of such cells.

iPS cells were first generated by Yamanaka and colleagues in 2006 from mouse fibroblast cells (*Cell* 126, 663-676). The method of deriving iPS cells traditionally involves the transfection of certain embryonic stem cell-associated genes into non-pluripotent cells, such as mature fibroblasts. Transfection is usually achieved through viral vectors, such as retroviruses. Yamanaka and colleagues initially identified 4 key genes essential for the production of pluripotent stem cells: Oct-3/4, Sox2, c-Myc and Klf4. Additional studies demonstrated the requirement of Nanog as another major determinant of cellular pluripotency (Okita et al., 2007; Wernig et al., 2007; and Maherali et al., 2007). In 2007, two independent research groups generated iPS cells from human cells (Takahashi et al., 2007; and Yu et al., 2007). Applying the same principles used earlier in mouse cells, Yamanaka and colleagues (Takahashi et al., 2007) successfully transformed human fibroblasts into pluripotent stem cells using the same 4 pivotal genes Oct-3/4, Sox2, c-Myc and Klf4 in a retroviral transfection system. Thomson and colleagues (Yu et al., 2007) used Oct4, Sox2, Nanog and Lin28 using a lentiviral transfection system. The exclusion of c-Myc in these experiments was based on evidence that c-Myc is oncogenic and is not necessary to promote cellular pluripotency.

Alternatively, and as self-renewing stem cells also exist in adult tissues buffered within specialised niches, a further approach would be to identify a pluripotent stem cell population which can conveniently be harvested without detriment to a donor. Stem cells have been isolated from a wide range of adult tissues, from those that have a high rate of ongoing cellular turnover, such as blood, cord blood, bone marrow, skin, intestine, and breast tissue, to those with a low turnover such as brain, skeletal muscle, and juvenile teeth.

However, most adult self-renewing stem cells only escape their quiescent state in response to developmental and physical cues in order to maintain homeostasis during tissue turnover or injury (Bjornson et al., 1999) and, as such, are generally only found in populations of very limited numbers. Further, it was thought that adult stem cells have limited differentiation potential restricted to the tissue/organ of origin. However, recent evidence has suggested that certain cell subpopulations within adult stem cell compartments are capable of in vitro and in vivo differentiation into cell types unrelated to their developmental origin (Clarke et al., 2000; Krause et al., 2001; Jiang et al., 2002; Hoffman, 2007). Notwithstanding, so far only a few such cell populations have been identified and the pluripotent cells obtained are often very limited in number rarely allowing direct therapeutic application of the cells. Great research efforts are now being directed at establishing methods of expansion of such cell populations without compromising the cells' pluripotent properties and therefore their differentiation potential.

In light of the above, it is noteworthy that bi-potent stem cells (Mammary gland stem cells; MaSCs) have been identified in the mammary gland and are known to exist in the basal epithelial layer in the resting breast. Interestingly, these cells have been shown to be capable of differentiation, however, only towards the two main mammary cell lineages, the myoepithelial and luminal cell lineages (Dontu et al., 2003; Shackleton et al., 2006; Villadsen et al., 2007; Visvader, 2009).

The mammary gland undergoes significant remodelling during pregnancy and lactation, which is fuelled by controlled mammary stem cell (MaSCs) proliferation. Briefly, while rudimentary mammary glands exist in males and females, hormonal changes during puberty lead to further development in females mainly through the influence of oestrogen and progesterone leading to the establishment of a rudimentary duct structure with terminal end bud formation. While, influenced by progesterone and prolactin levels, the duct structure of the mammary gland is further refined following puberty, secretory alveoli only develop during pregnancy. The gland finally develops into a secretory, milk producing organ during late pregnancy and/or in the first few days after birth with the secretion of colostrum. Colostrum production is followed by a short period of production of the so called "transition milk" leading to the production of mature milk throughout the lactation period. After weaning, the mammary gland undergoes involution during which the developmental stages seen during gestation are reversed such that the mammary gland reverts to a near resting state. From the above, it will be appreciated that the mammary gland is a highly plastic organ capable of intense remodelling during repeated pregnancies during the life of a female.

The lactating breast in its fully mature state displays the complete cellular hierarchy and contains a larger number of stem cells than found in the resting breast. It is therefore thought that the lactating breast provides the best model for studying the properties of MaSCs. However, due to the scarcity of human lactating breast tissue specimens the human lactating breast has not been extensively studied in this context. As such, the scarcity of human lactating breast tissue specimens and the low number and quiescent state of MaSCs in available resting breast tissue specimens have hindered understanding of the normal MaSC biology and the molecular determinants that drive their aberrant self-renewal in breast cancer.

The existence of stem cells in the breast was first postulated based on the capacity of the mammary epithelium to significantly expand and regress in a repeated fashion throughout adult life (Taylor-Papadimitriou et al., 1977). In accordance with this hypothesis, and as known for other adult stem cell populations, MaSCs exist in a quiescent state and in scarce numbers in the resting breast. Yet, due to the physiological changes linked to mammary remodelling during pregnancy and lactation, MaSCs appear to undergo a controlled program of proliferation, differentiation, and apoptosis stimulated by hormonally-driven cues (Pang and Hartmann, 2007; Asselin-Labat et al., 2010; Joshi et al., 2010).

However, in addition to their important physiological role during pregnancy and lactation, increasing evidence also implicates MaSCs in the onset and progression of invasive breast carcinomas having metastatic features with a propensity towards both mesodermal (bone) and endodermal (lung) organs. It would therefore appear that the mammary gland harbours a stem cell population with unique self-renewal capabilities and a potential plasticity reflected both in normal development and in aberrant conditions of the breast. To date, and despite ongoing research in this field, our understanding of normal MaSC biology is limited and the molecular determinants and regulators of MaSC self-renewal and plasticity (normal or aberrant) are largely unknown.

Currently a lack of suitable cell culture model systems for propagation and characterisation of MaSCs exists and progress has been hindered twofold, (a) by the scarcity and quiescent state of MaSCs obtainable from the resting breast, and (b) by the extremely limited availability of human lactating breast tissue, which contains activated MaSCs in greater numbers.

Interestingly, it has also been shown that breastmilk contains a mixture of different cell types such as, for example, epithelial cells (lactocytes). It would appear that these cells are sloughing off the basement membrane of the breast as a consequence of the pressure and shear forces associated with the continued filling and emptying of the breast and, as a result infiltrate the milk. It has been stipulated that lactocytes account for approximately 10-20% of the total cell population (varying significantly between individual breastmilk samples). While it has long been thought that the majority of the remainder of cells found in human milk are immune cells (such as lymphocytes, macrophages, monocytes, natural killer cells, basophils, eosinophils, and neutrophils) more recent data suggests that human breastmilk from healthy subjects only contains a small percentage of immune cells.

In addition to lactocytes and immune cells, it has previously been demonstrated that breastmilk also contains an activated MaSC population derived from the lactating breast and that this cell population can be accessed non-invasively via expressed breastmilk (Cregan et al., 2007; Thomas et al., *Cell Cycle*, 2011; Thomas et al., *Cell Death Dis.*, 2011). MaSCs as well as the differentiated cells from the lactating epithelium mentioned above enter breastmilk either through cell migration and turnover and/or as a consequence of the mechanical shear forces of breastfeeding. Culture of $CD49f^+$, human breastmilk-derived multipotent cells expressing the epithelial stem cell marker p63 in epithelial-specific two-dimensional (2D) monolayer culture over a twenty-one day period showed that a non-adherent, multipotent $p63^+$ epithelial cell population expands in the floating cell population within the first five days of growth. However, these cells are depleted reciprocally with attachment and expansion of adherent cells homogenously expressing pan-epithelial markers. In the proceeding sixteen days of growth subpopulations of adherent cells expressing myoepithelial and luminal epithelial markers in mutually exclusive colonies have been identified, indicating that lineage commitment has already occurred in the floating cell population prior to adherence. Furthermore, when the adherent cells are subsequently cultivated in a three-dimensional (3D) biomatrix, these cells have been shown to form differentiated spherical, milk protein-secreting structures (mammospheres) resembling the in vivo secretory alveoli. Based on these results, it would appear that the $p63^+/CD49f^+$ cell population in breastmilk shares properties of MaSCs (Thomas et al., *Cell Cycle*, 2011; Thomas et al., *Cell Death Dis.*, 2011). As such, these results indicate that breastmilk contains MaSCs capable of differentiation towards the myoepithelial and luminal mammary lineages.

As indicated above, it has long been known that breastmilk contains a mixture of different cell types. However, a comprehensive analysis and characterisation of human milk identifying all different cell types found in breastmilk is still needed.

In light of the above, it will be appreciated that there is a need in the art for improved methods of isolating embryonic stem cell-like (pluripotent) cell populations from adult tissues/organs as well as for improved methods of propagation and expansion of any such cells with a view to producing cell numbers suitable for therapeutic application.

SUMMARY OF THE INVENTION

The present invention overcomes or ameliorates at least one of the disadvantages of the prior art, or to provide a useful alternative. The studies underlying the present invention were aimed to examine whether breastmilk contains stem cell populations with a wide ranging differentiation potential allowing for differentiation towards cell types outside the mammary lineage.

In a first aspect the present invention relates to a method of preparing a breastmilk stem cell(s) (BSC) or a spheroid comprising or consisting of BSC, comprising the steps of:
a) separating cells from non-cellular portions of breastmilk obtained from a subject, wherein said cells comprise a mixture of cells;
b) growing the mixture of cells in suspension culture to form one or more spheroids; and
c) harvesting said one or more spheroids, wherein said one or more spheroids comprise or consist of said BSC.

Generally, the step of growing said mixture of cells comprises the proliferation of a cell. The step of growing said mixture of cells typically comprises selective proliferation of said BSC.

In some embodiments, the at least one spheroid is harvested after growing in suspension culture for up to 12-14 days. Typically, the at least one spheroid is harvested after growing in suspension culture for 9 days.

In some embodiments, the method of the first aspect further comprising the step of passaging the at least one spheroid in suspension culture after step (b) and before step (c). The passaging comprises dissociation of said at least one spheroid.

In some embodiments, the at least one spheroid is grown in a low-binding cell culture vessel. Typically, the at least one spheroid is grown in a feeder-free culture.

In some embodiments, the step of growing the mixture of cells in suspension culture comprises growing the cells in the presence of any one or more of the following, or combinations thereof: growth factors, insulin, transferrin, selenium, nicotinamide, dexamethasone, fetal bovine serum or non-essential amino acids (NNEA). The growth factors are selected from epidermal growth factor and fibroblast growth factor.

In some embodiments, the BSC is a pluripotent stem cell.

In some embodiments, the breastmilk is human breastmilk and the BSC is a human pluripotent stem cell. The human BSC (hBSC) expresses Oct4, Sox2, Nanog and/or Klf4.

In a second aspect the present invention relates to a method of preparing breastmilk stem cell(s) (BSC) or a spheroid comprising or consisting of BSC, comprising the steps of:
a) separating cells from non-cellular portions of breastmilk obtained from a subject after initiation of feeding, wherein said cells comprise a mixture of cells;
b) growing the mixture of cells in suspension culture to form one or more spheroids; and
c) harvesting said one or more spheroids, wherein said one or more spheroids comprise or consist of said BSC.

In some embodiments, the breastmilk is obtained after or at the end of said feeding. Typically, the breastmilk is obtained from about 0 minutes to about one hour after said feeding. Alternatively, the breastmilk is obtained about 25-30 minutes after said feeding.

In one or more embodiments, the BSC is differentiated to become a myoepithelial cell, a luminal cell, a lactocyte, a neural cell, a stromal cell, an osteoblast, a chondrocyte, an adipocyte, a cardiomyocyte, a hepatocyte, or a beta islet cell.

In a third aspect the present invention relates to breastmilk stem cell(s) (BSC) or a spheroid comprising or consisting of BSC prepared according to the methods of the first or second aspect.

In some embodiments, the BSC is a pluripotent stem cell.

In a fourth aspect the present invention relates to breastmilk stem cell(s) (BSC) or a spheroid comprising or consisting of BSC prepared according to the methods of the first or second aspect, wherein said cell has low tumorigenicity and does not form teratomas.

In a fifth aspect the present invention relates to isolated breastmilk stem cell(s) (BSC), wherein said BSC is a pluripotent stem cell or a progenitor or a more committed cell.

In some embodiments, the BSC is capable of differentiating or has differentiated to become a myoepithelial cell, a luminal cell, a lactocyte, a neural cell, a stromal cell, an osteoblast, a chondrocyte, an adipocyte, a cardiomyocyte, a hepatocyte, or a beta islet cell In a sixth aspect the present invention relates to a composition comprising the cell or the spheroid comprising or consisting of BSC of the third, fourth or fifth aspect.

In a seventh aspect the present invention relates to method of cell treatment in a patient in need thereof comprising administering to said patient an effective amount of the cell or the spheroid comprising or consisting of the BSC of the third, fourth or fifth aspect or the composition of the sixth aspect.

In an eighth aspect the present invention relates to a method of treating milk production deficiency in a lactating female in need thereof comprising administering to said female the cell or the spheroid comprising or consisting of the BSC of the third, fourth or fifth aspect or the composition of the sixth aspect in an amount effective to treat said milk production deficiency.

In some embodiments, the cell administered in the methods of the sixth or seventh aspect is autologous to the patient. Alternatively, the patient is an infant and the cell is obtained from the breastmilk of the infant's mother.

In a ninth aspect the present invention relates to a method of treating a disease condition in a patient in need thereof comprising the step of administering to the patient an effective amount of the cell or the spheroid comprising or consisting of the BSC of the third, fourth or fifth aspect or the composition of the sixth aspect, wherein the disease condition is a cardiovascular disease, diabetes, inborn errors in metabolism, cancer, a neurological disease, a chronic disease, a liver disease, a fatal infant disease, or any organ/tissue disease for which administration of said cell is beneficial.

Reference throughout this specification to "one embodiment", "some embodiments" or "an embodiment" means that a particular feature, structure or characteristic described in connection with the embodiment is included in at least one embodiment of the present invention. Thus, appearances of the phrases "in one embodiment", "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

In the context of this specification the following terms are defined as follows:

"comprising"—Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

"lineage"—In so far as this term refers to cell lineages, a lineage is a genealogic pedigree of cells related through mitotic division.

"lineage-specific"—In so far as this term refers to cells, it refers to the differentiation state to which a cell has become committed.

"progenitor/precursor cell"—Please note that these terms can be used interchangeably and, in so far as the terms refer to cells, they refer to a cell capable of differentiating into a number of cell and/or tissue types of a cell lineage.

"pluripotent"—In so far as this term refers to cells, it refers to a cell capable of differentiating into cell and/or tissue types of all cell lineages, excluding extra embryonic cell and/or tissue types.

"multi-potent"—In so far as this term refers to cells, it refers to a cell capable of differentiating into of cell and/or tissue types of multiple but not all cell lineages.

"milk production deficiency"—In so far as this term refers to a condition suffered by lactating female, it relates to females who cannot produce breastmilk at all as well as to females-who have insufficient breastmilk supply.

Also, the terms 'a', 'an' and 'the' mean 'one or more', unless expressly specified otherwise. The terms 'an embodiment', 'embodiment', 'embodiments', 'the embodiment', 'the embodiments', 'some embodiments', 'an example embodiment', 'at least one embodiment', 'one or more embodiments' and 'one embodiment' mean 'one or more (but not necessarily all) embodiments of the present invention(s)' unless expressly specified otherwise. For example, reference to "a cell" includes a single cell as well a mixture or combination of two or more cells. Similarly, reference to "a growth factor" includes mixtures of two or more growth factors as well as a single growth factor, and the like.

BRIEF DESCRIPTION OF THE DRAWINGS

Embodiments of the invention will now be described, by way of example only, with reference to the accompanying drawings in which:

FIG. 2C shows the presence of the selected cell markers in breast tissue using immunofluorescent staining.

FIGS. 4A through 4D illustrate the presence of cells expressing embryonic stem cell (ESC) markers in hBSC preparations.

DESCRIPTION OF THE INVENTION

Figure 1A:
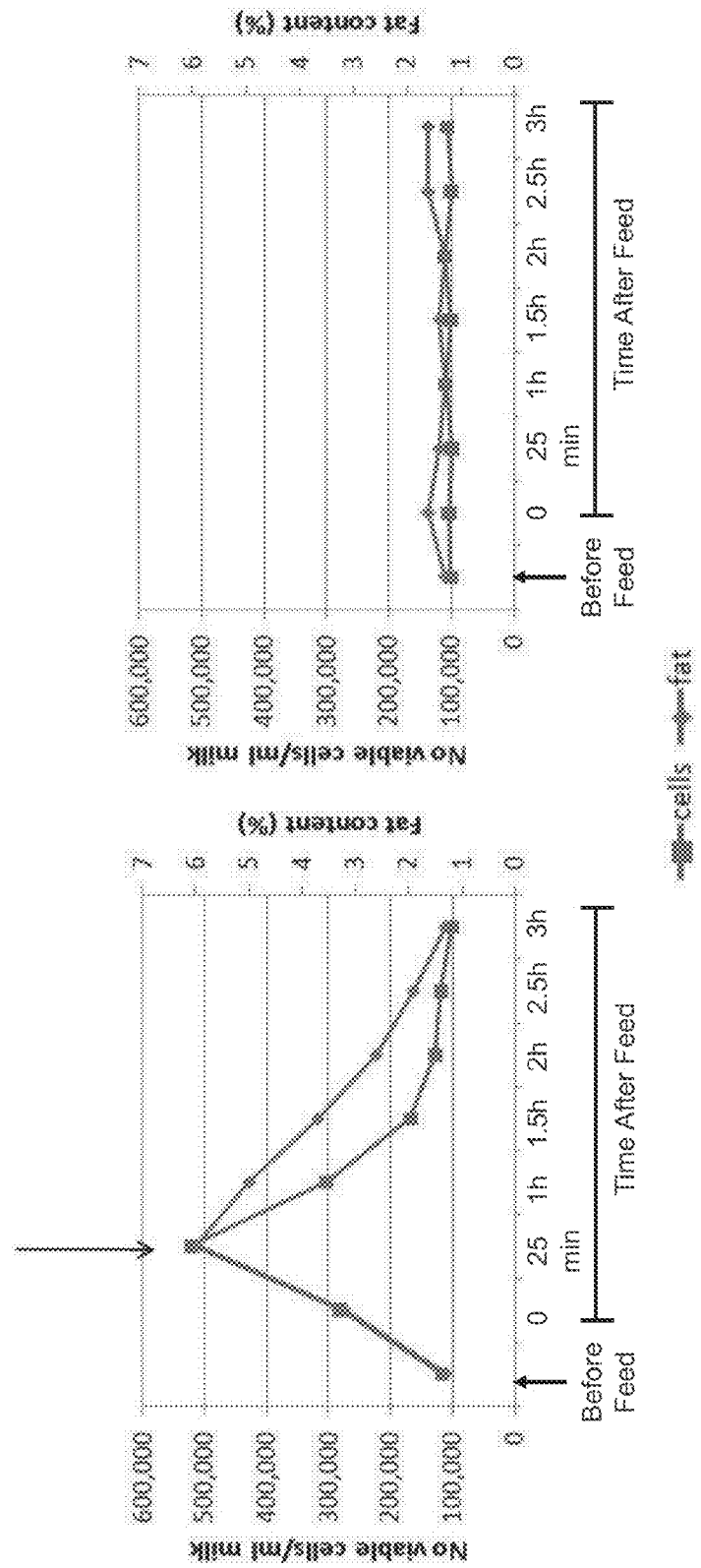
FIG. 1A and FIG. 1B illustrate the total amount of cells found in breast milk over a time course following feeding.
Figure 1B:
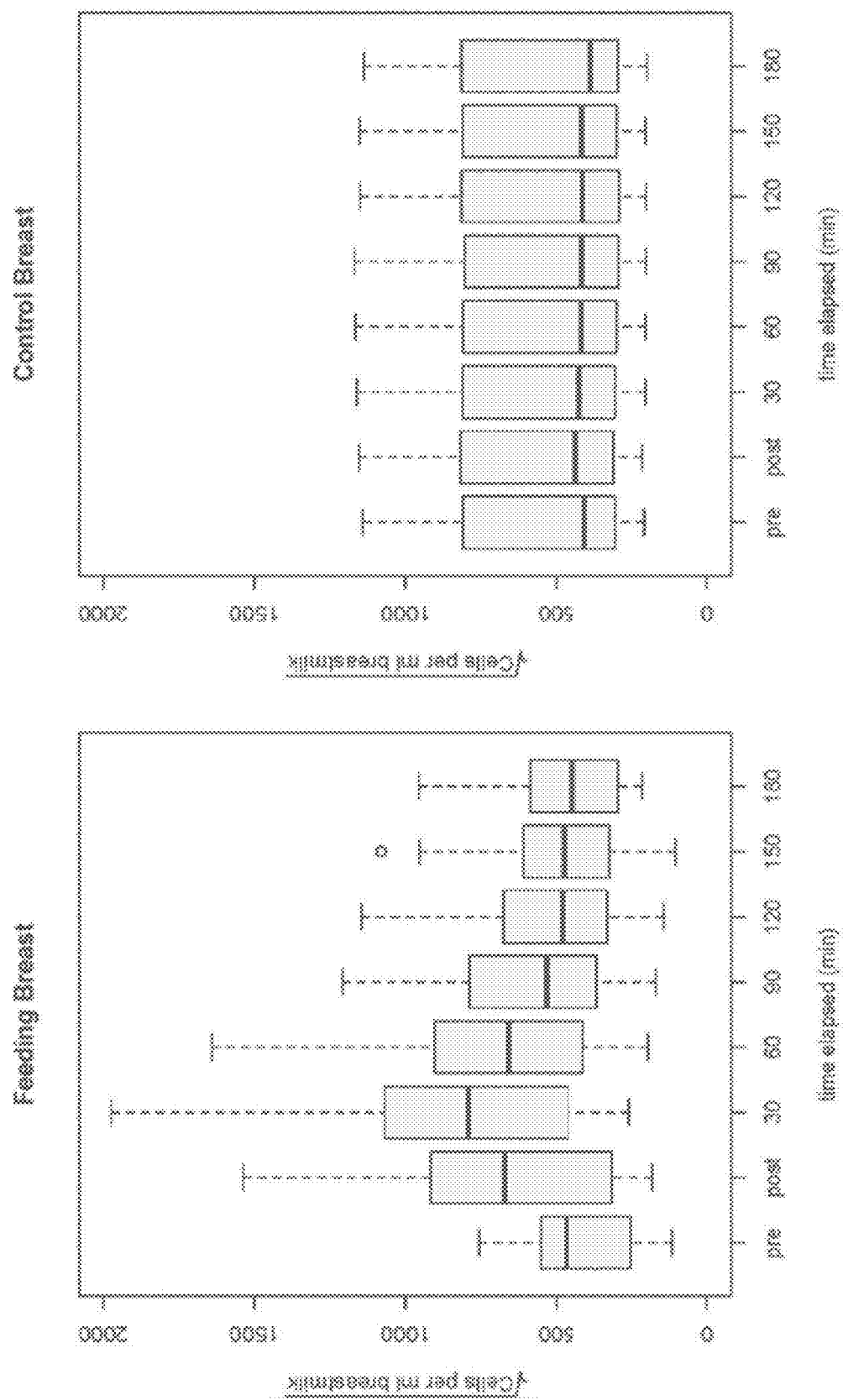

Surprisingly, it was found that a stem cell population exists in breastmilk (breastmilk stem cells; BSCs), which expresses an array of genes responsible for the regulation of pluripotency in embryonic stem cells (ESCs or ES cells) such as, for example, the genes for the transcription factors (TFs) Oct4, Sox2, Nanog and Klf4.

In situ histological examination of rare human lactating breast tissue specimens revealed the origin and localisation in the lactating breast epithelium of this hBSC population. By contrast, this cell population was scarce in normal resting breast tissue biopsies. Upon expansion in feeder cultures in ESC growth conditions, hBSCs exhibited the encapsulated ESC-like colony morphology and phenotype. These colonies could be passaged in secondary feeder cultures, demonstrating clonogeneicity and self-renewal.

Propagation of hBSCs in 3D culture conditions resulted in the formation of spheroids with a dramatic up-regulation of ESC TFs. Furthermore, hBSCs differentiated in vitro into cell types from all three germ layers, and they did not form tumors when injected in mice. These findings demonstrate that breastmilk is a novel and non-invasive resource of patient-specific stem cells with ESC-like properties. This cell population is easily accessible and may be used in regenerative medicine and to study molecular determinants of cancer.

Materials & Methods

Breastmilk Sample Collection

The study was approved by the Human and Animal Research Ethics Committees of The University of Western Australia and the University of North Carolina, and all participants provided informed written consent. Healthy breastfeeding women (>70) were recruited in Australia and USA, covering a wide range of lactation stages, from month 1 to year 5 and beyond. Pump-expressed mature breastmilk was obtained from each participant and was transported to the laboratory immediately upon expression under aseptic conditions.

Breastmilk Cell Isolation

Breastmilk was diluted with equal volume of sterile PBS (pH 7.4, Gibco, USA) and centrifuged at 805 g for 20 min at 20° C. The fat layer and liquid part were removed with a pipette and the cell pellet was washed three times in PBS and was resuspended in 7% Fetal Bovine Serum (FBS, Certified, Invitrogen, USA) in PBS (blocking buffer). The total cell concentration and viability of each sample were determined with a Neubauer hemocytometer by Trypan Blue exclusion.

Cell Culture

The human embryonic stem cell line H7 was maintained at 37° C. and 5% $CO_2$ in hESC medium containing DMEM/F12 (Gibco), 20% knock-out serum replacement (Invitrogen), 5 ng/ml human basic fibroblast growth factor (bFGF, Sigma-Aldrich), 100 µM non-essential amino acids (NEAA, Invitrogen), 100 µM β-mercaptoethanol (Sigma-Aldrich), and 5% antibiotic/antimycotic (Invitrogen), and 2 µl/ml fungizone (Invitrogen). Immortalized mammary epithelial cells from resting breast mammoplasties were maintained in HuMEC complete medium (Invitrogen). Primary neonatal human fibroblasts were cultured in DMEM (Gibco) supplemented with 10% fetal bovine serum (FBS, Invitrogen) and 1% antibiotic/antimycotic (Invitrogen). For feeder culture of breastmilk cells, plates were coated with 0.01% gelatine at 37° C. for 40 min. Unbound gelatine was aspirated off and washed out with PBS prior to seeding of MEFs. MEFs were maintained in DMEM (Gibco) containing 10% FBS (Invitrogen) and 1% antibiotic/antimycotic (Invitrogen). Two hours prior to plating of breastmilk cells, the MEF medium was aspirated off, the plate was washed with PBS and fresh hESC medium was added. Breastmilk cells were seeded in feeders in MEF-conditioned hESC medium at densities ranging $5 \times 10^5$-$5 \times 10^6$ per 35 mm dish and incubated at 37° C. and 5% $CO_2$. On days 2 and 4 after plating, fresh hESC medium was added on top of the existing medium. On day 5-6, the medium was changed, and since then medium change was done daily. For secondary feeder culture, single colonies were individually picked and transferred to new plates in appropriate volume of fresh medium in a split ratio of 1:2. For feeder-free culture, breastmilk cells were seeded in gelatine-coated or uncoated adherence plates in hESCs medium at densities ranging $5 \times 10^5$-$5 \times 10^6$ per 35 mm dish, and incubated at 37° C. and 5% $CO_2$. Media changes were done as above. For passaging of the adherent colonies, the cells were washed once with PBS and then incubated with trypsin medium (Gibco) for 5 min at 37° C. Detached cells were collected after addition of trypsin inhibitor (Invitrogen), washed with PBS once, resuspended in fresh medium and transferred to a new plate in a split ratio of 1:3. For spheroid culture, breastmilk cells were seeded in ultra-low binding plates (Co-Star) at densities ranging $5 \times 10^5$-$5 \times 10^6$ per 35 mm dish, in MammoCult medium (Stem Cell Technologies) supplemented with 3% antibiotic/antimycotic and 2 µl/ml fungizone (Invitrogen). Spheroids were maintained for up to 2 weeks at 37° C. and 5% $CO_2$ with addition of fresh MammoCult medium on top of the existing medium every 3 days. For spheroid passaging, spheroids were washed once with PBS and then incubated with trypsin medium (Gibco) for 5 min at 37° C. Dissociated cells were collected after addition of trypsin inhibitor (Invitrogen), washed with PBS once, resuspended in fresh medium and transferred to a new plate in a split ratio of 1:3.

Flow Cytometry

Antibodies against ESC markers were standardised using human fibroblasts as negative control (FIG. 4) and were shown to recognize their target proteins by FACS (Stemgent, USA Santa Cruz Biotechnology, USA). Freshly isolated breastmilk cells were incubated in unconjugated or fluorophore-conjugated primary antibody (see Table 1 below) for 30 min at 4° C., followed by washes and secondary antibody incubation (for unconjugated primaries) for 30 min at 4° C. (AlexaFluor, Invitrogen, USA), and finally washed and resuspended in fixative (1% paraformaldehyde/0.7% sucrose in PBS). For surface markers, all incubations and washes were done in blocking buffer, while for intracellular markers in 0.05% Tween-20 in PBS after initial cell fixation. Cells were also incubated with live/dead fixable cell stain (Invitrogen, USA) according to the manufacturer's instructions and only the live cells were included in data analyses. Appropriate negative and isotype controls were used. Data acquisition was done with a FACS Calibur Flow Cytometer (Becton Dickinson, New Jersey, USA) and data analysis with FlowJo. Cell debris were excluded from the analyses, via propidium iodide staining (Sigma-Aldrich) at 1 µg/ml.

Quantitative Real-Time Polymerase Chain Reaction

Total RNA from freshly isolated breastmilk cells, harvested hBSC-derived spheroids, hESC H7 cell line, mammary immortalised cells derived from resting tissue mammoplasties, and human primary neonatal fibroblasts was extracted with an RNeasy extraction kit (Qiagen, Valencia, Calif., USA) following the instructions of the manufacturer.

Total RNA was reverse-transcribed using the high-capacity cDNA archive kit (Applied Biosystems, Carlsbad, Calif., USA) plus RNase inhibitor (Applied Biosystems). Gene transcription was quantified by qRT-PCR using hydrolytic probes (Taqman; Applied Biosystems) with the 7500 Fast RT-PCR system (Applied Biosystems). Fold change in gene expression for each sample and experimental condition was calculated as $2^{Ct(control)-Ct(sample)}\pm$standard deviation.

Western Blotting

Freshly isolated breastmilk cells, hBSC-derived spheroids, hESCs (positive control) and primary neonatal human fibroblasts (negative control) were lysed in RIPA buffer for 30 min on ice. Protein was quantified using the Micro BCA protein kit (Thermo Scientific). Protein denaturation was done for 5 min at 95° C. 50 μg of protein were loaded into Biorad TGX stain-free gels, which were run at 300 V for 30 min. Protein was transferred onto membranes using a Trans-Blot Turbo System (Biorad). Membranes were washed in 0.05% TBS-T, stained with Ponceau red for 5 min, destained with dH2O, and washed in 0.05% TBS-T. Membranes were blocked using 5% non-fat cow's skim milk for 1 hour, incubated with primary antibodies (Table 1) overnight at 4° C., washed in 0.05% TBS-T, and incubated with secondary antibodies with 1:10,000 Streptoactin for 1 hour at room temperature. Subsequently, membranes were washed in 0.05% TBS-T before incubation in Chemiluminescence Crescendo (Millipore) for 5 min. Imaging was done using a Chemi-Doc MP (Biorad). Culture supernatants from breastmilk cells cultured under mammary differentiation conditions were harvested on weeks 2-4 of culture and examined for the presence of α-lactalbumin and lactoferrin. Fresh medium and human breastmilk/purified proteins were used as negative and positive controls, respectively. 200 μg of total protein from the culture supernatants was loaded per well of a 10% polyacrylamide gel and run under SDS/PAGE denaturing conditions. Antibodies were applied at the concentrations listed in Table 1. Proteins were transferred to a nitrocellulose membrane and blocked for 1 hour in 5% cow's skim milk. Membranes were then developed (ECL-Plus, GE Healthcare, Piscataway, N.J., USA) and visualized by autoradiography.

In Vitro Differentiation

To examine the ability of hBSCs to spontaneously differentiate, breastmilk cells were initially grown as spheroids (see above). By day 4-7, some cells had attached. The remaining spheroids were then transferred into new wells where adherent cells appeared in 1-2 days. Both the initial and subsequent attached cells were cultured for another 2-3 weeks, with media changes every 5 days. For directed differentiation, primary and first- to third-passage breastmilk cell cultures were incubated in corresponding differentiation media for 3-4 weeks. For mammary differentiation, cells were incubated at 37° C. and 5% $CO_2$ in medium containing RPMI 1640 with L-glutamine (Invitrogen) supplemented with 20% FBS (Certified, heat-inactivated, Invitrogen), 4 μg/ml insulin (Invitrogen), 20 ng/ml EGF (Invitrogen), 0.5 μg/ml hydrocortisone (Sigma-Aldrich), 60 ng/ml cholera toxin (Sigma-Aldrich), 5% antibiotic-antimycotic (Invitrogen), and 2 μl/ml fungizone (Invitrogen). For osteoblastic and adipogenic differentiation, cells were incubated for 3-4 weeks in NH OsteoDiff or NH Adipodiff medium, respectively, (Miltenyi Biotec), with 5% antibiotic-antimycotic and 2 μl/ml fungizone. For chondrocyte differentiation, cells were incubated for 3-4 weeks in StemPro Chondrogenesis Differentiation medium (Life Technologies). For neuronal differentiation, cells were incubated in RPMI 1640 with L-glutamine, supplemented with 20% FBS, 4 μg/ml insulin, 20 ng/ml EGF, 0.5 μg/ml hydrocortisone, 5% antibiotic-antimycotic, 2 μl/ml fungizone, 20 ng/ml prolactin (Peprotech), and MACS Supplement B27 (Miltenyi Biotec). For hepatocyte differentiation, cells were cultured in Williams' E basic medium supplemented with 10% FBS, 2.5 μg/ml fungizone, 5% antibiotic/antimycotic (Invitrogen), 2 mM glutamine (Sigma-Aldrich), 6.25 μg/ml ITS (growth supplement comprising insulin, transferring and selenium; Invitrogen), 20 ng/ml EGF (BD Biosciences), 10 mM nicotinamide, and $10^{-7}$ M dexamethasone for 2-4 weeks. For pancreatic differentiation, cells were first incubated for 2 days in high-glucose DMEM supplemented with 10% FBS, 2.5 μg/ml fungizone, 5% antibiotic/antimycotic (Invitrogen), 2 mM glutamine (Sigma-Aldrich), 6.25 μg/ml ITS (Invitrogen), 20 ng/ml EGF (BD Biosciences), 50 ng/ml activin A (Sigma-Aldrich), and $10^{-6}$ mol/l retinoic acid (Sigma-Aldrich). Subsequently, for the next 9-12 days cells were incubated in DMEM/F12 supplemented with 10% FBS, 2.5 μg/ml fungizone, 5% antibiotic/antimycotic (Invitrogen), 2 mM glutamine (Sigma-Aldrich), 6.25 μg/ml ITS (Invitrogen), 20 ng/ml EGF (BD Biosciences), 10 mM nicotinamide, $10^{-7}$ M dexamethasone, and 300 nmol/l indolactam V (Sigma-Aldrich). For the final 2-4 days of differentiation, the above medium was used supplemented with 50 ng/ml activin A. For cardiomyocyte differentiation, cells were cultured in DMEM/F12 supplemented with 20% FBS, 5% horse serum (Invitrogen), 2 mM L-glutamine, 0.1 M NEAA, 3 mM sodium pyruvate (Invitrogen), 1 μg/ml insulin, 2.5 μg/ml fungizone, and 5% antibiotic/antimycotic.

Mammary Tissue Sections

Lactating and resting mammary tissue sections (5 μm-thick) were prepared from normal human biopsied formalin-fixed and paraffin-embedded tissue currently available in the tissue archive of the School of Anatomy and Human Biology, The University of Western Australia (n=6).

Immunohistochemistry

Antibodies for ESC markers were standardised using human fibroblasts as negative control cells (FIG. 4). All antibodies used were shown to recognize their target proteins by immunocytochemistry (Table 1). Part of the breastmilk cell suspensions was immediately fixed for immunofluorescence staining in 1.5% paraformaldehyde/0.7% sucrose in PBS and cytospins of the cell suspensions on glass slides were generated using a Shandon Cytospin 3 centrifuge at 40.7 g for 4 min. Primary antibodies (Table 1) were applied in blocking buffer for 1 hour at room temperature in a humid chamber, after a 5-min permeabilisation with 0.05% Tween20 in PBS for intracellular markers. Appropriate controls were used. The cytospins were washed in PBS and incubated with secondary antibody (AlexaFluor 488, 546 or 555 nm, Invitrogen) in blocking buffer at 1:300 and DAPI (1:100, Roche) for 30 min. After a final wash, they were mounted in DakoCytomation fluorescent mounting medium. Fixed adherent cells grown on plastic plates were stained after 10-25 days of growth. Adherent cells grown on plastic plates were fixed as above, permeabilised in 0.1% TritonX in PBS for 30 min, washed in PBS, incubated with primary and secondary antibodies as above, washed and resuspended in fixative. Mammary tissue sections were rehydrated in deionised water overnight at 4° C., followed by a 10-min incubation in PBS, permeabilisation in 0.1% PBS-TritonX 100 for 15 min under humid conditions, and a wash in PBS prior to overnight incubation in at room temperature with primary antibody (Table 1) in blocking buffer. Negative control sections were also prepared. The sections were then washed in PBS and incubated with secondary antibody (as above) for 2 hours, followed by a final wash and mounting. Appropriate negative controls (with no primary antibody incubation) were used to standardise imaging, which was done using a Nikon A1Si and in R 2.9.01 (R Development Core, 2009). The results are presented as mean±SEM as indicated in figure legends, and P values are shown in the figures.

TABLE 1

Markers tested and corresponding antibodies used.

| Marker | Company | Cat. No | Applications used |
|---|---|---|---|
| Oct4 | Miltenyi (Stemgent) | 130-095-635 | FACS (1:100), IF (1:100), IHC (1:100) |
| Oct4A | Santa Cruz Biotech. | sc-5279 | FACS (1:50), IF (1:100), IHC (1:100) |
| Oct4 | Abcam | ab18976 | IF (1:100) |
| Oct4A | Cell Signalling Tech. | 2840 | WB (1:1000) |
| Sox2 | Miltenyi (Stemgent) | 130-095-636 | FACS (1:50), IF (1:50), IHC (1:50) |
| Sox2 | Cell Signalling Tech. | 3579 | IF (1:100), WB (1:1000) |
| Nanog | Santa Cruz Biotech. | sc-33759 | FACS (1:100), IF (1:100), IHC (1:100) |
| Nanog | Abcam | ab80892 | IF (1:100) |
| Nanog | R&D Systems | AF1997 | IF (1:50) |
| Nanog | Cell Signalling Tech. | 3580 | WB (1:1000) |
| SSEA4 | Miltenyi (Stemgent) | 130-095-622 | FACS (1:100), IF (1:100), IHC (1:100) |
| SSEA4 | Hybridoma cell line* | MC-813-70 | IF (1:30) |
| Tra-1-60 | Miltenyi (Stemgent) | 130-095-625 | FACS (1:300), IF (1:300), IHC (1:300) |
| Tra-1-60 | ABCAM | ab16288 | IF (1:100) |
| Tra-1-81 | Miltenyi (Stemgent) | 130-095-626 | FACS (1:300), IF (1:300), IHC (1:300) |
| Tra-1-81 | ABCAM | ab16289 | IF (1:100) |
| β-actin | Sigma-Aldrich | A5441 | WB (1:1000) |
| CK14 | AbD Serotec | SEMCA890HT | IF (1:100) |
| α-SMA | Sigma-Aldrich | A2547-0.2ML | IHC (1:100) |
| CK18 | Abcam | ab32118 | IF (1:100) |
| β-casein | AbD Serotec | SE18602655 | IF (1:20) |
| β-casein | Santa Cruz Biotech. | sc-53189 | IF (1:100) |
| α-lactalbumin | Dako | A057901 | WB (1:500) |
| lactoferrin | MP Biomedicals | 670581 | WB (1:500) |
| β-III-tubulin | Covance | PRB-435P | IF (1:1000) |
| Nestin | Miltenyi (Stemgent) | 130-095-648 | IF (1:100) |
| OV6 | R&D Systems | MAB2020 | IF (1:200) |
| M2PK | Cell Signalling Tech. | 3198 | IF (1:200) |
| α-Fetoprotein (AFP) | ZYMED Laboratories | 18-0055 | IF (1:200) |
| Albumin | Sigma-Aldrich | A-3293 | IF (1:200) |
| PDX1 | Santa Cruz Biotech. | sc-14662 | IF (1:100) |
| PDX1 | Cell Signalling Tech. | 2437S | IF (1:100) |
| Insulin | Santa Cruz Biotech. | sc-52040 | IF (1:100) |
| Insulin | Cell Signalling Tech. | 4590S | IF (1:100) |
| RUNX2 | Santa Cruz Biotech. | sc-101145 | IF (1:100) |
| OSX | Santa Cruz Biotech. | sc-133871 | IF (1:100) |
| Sox6 | Santa Cruz Biotech. | sc-20092 | IF (1:100) |
| PPAR-γ | Santa Cruz Biotech. | sc-1984 | IF (1:100) |
| Vimentin | Sigma-Aldrich | V5255 | IF (1:100) |
| STRO-1 | Hybridoma cell line** | | IF (Culture supernatant) |
| Desmin | Sigma-Aldrich | D1033-0.2ML | IF (1:100) |
| Cardiac T troponin | Abcam | ab45932 | IF (1:100) |

FACS: Fluorescence Activated Cell Sorting;
IF: Immunofluorescence staining;
IHC: Immunohistochemistry;
WB: Western Blotting.
*Culture supernatant was purchased from the Development Studies Hybridoma Bank.
**The hybridoma cell line was purchased from the Development Studies Hybridoma Bank.

Confocal microscope, an Olympus TH4-200 inverted optical microscope, a Nikon Eclipse Ti inverted optical microscope and a Leica DMIRB Inverted Fluorescence/DIC microscope.

Teratoma Formation Assay

Freshly isolated breastmilk cells ($3 \times 10^6$-$32 \times 10^6$) or spheroid-derived breastmilk cells ($2 \times 10^5$-$10^7$) were suspended in 30% Matrigel (BD Biosciences, USA) in PBS and injected subcutaneously into dorsal flanks of 15 immunodeficient (SCID) mice. Nine weeks after injection, mice were examined for tumor formation. p86-OTBC-L1 (OCT4-tranduced breast cells) (Beltran et al., 2011) were used as positive control.

Statistical Analysis

All statistical analyses, including descriptive statistics, graphical exploration of the data, and Student's t tests for statistical significance were performed in Microsoft Excel and in R 2.9.01 (R Development Core, 2009). The results are presented as mean±SEM as indicated in figure legends, and P values are shown in the figures.

Results

Breastmilk Contains Different Number of Cells at Different Times

It has been found that the number of cells contained in breastmilk varies significantly. Specifically, and referring to FIGS. 1A and B, the amount of total cells in breastmilk samples sharply increases shortly after a feed, with a peak (maximum concentration at about 25 to 30 minutes following a feed and then gradually decreases back to the concentration of cells found just before feeding is initiated. Accordingly, most efficient sampling of breastmilk for cell collection should occur after feeding, more preferably within 1.5 hours following feeding and most preferably at about 25 to 30 minutes following feeding.

Figure 1C:
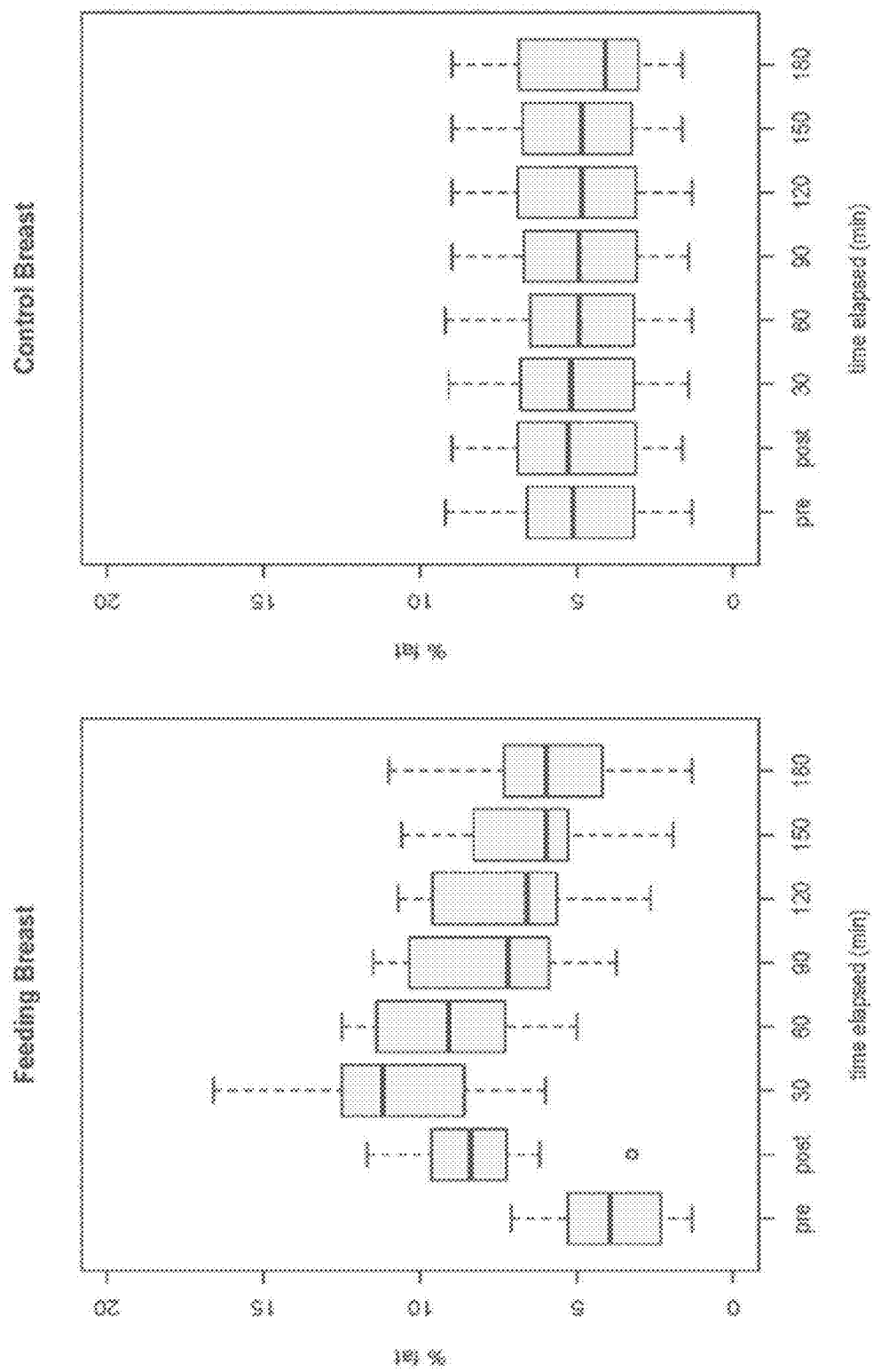
FIG. 1C shows the fat concentration of breastmilk over a similar time course.

Interestingly, and as shown in FIG. 1C, it has also been found that the overall fat concentration of breastmilk follows the pattern described above with respect to cell concentration. Accordingly, the fat concentration also sharply increases shortly after a feed, with a peak (maximum concentration at about 25 to 30 minutes following a feed). Again, and as seen for the number of cells found in breastmilk, the fat concentration then gradually decreases to the concentration found just before feeding is initiated.

Characterisation of Breastmilk Cells

Figure 2A:
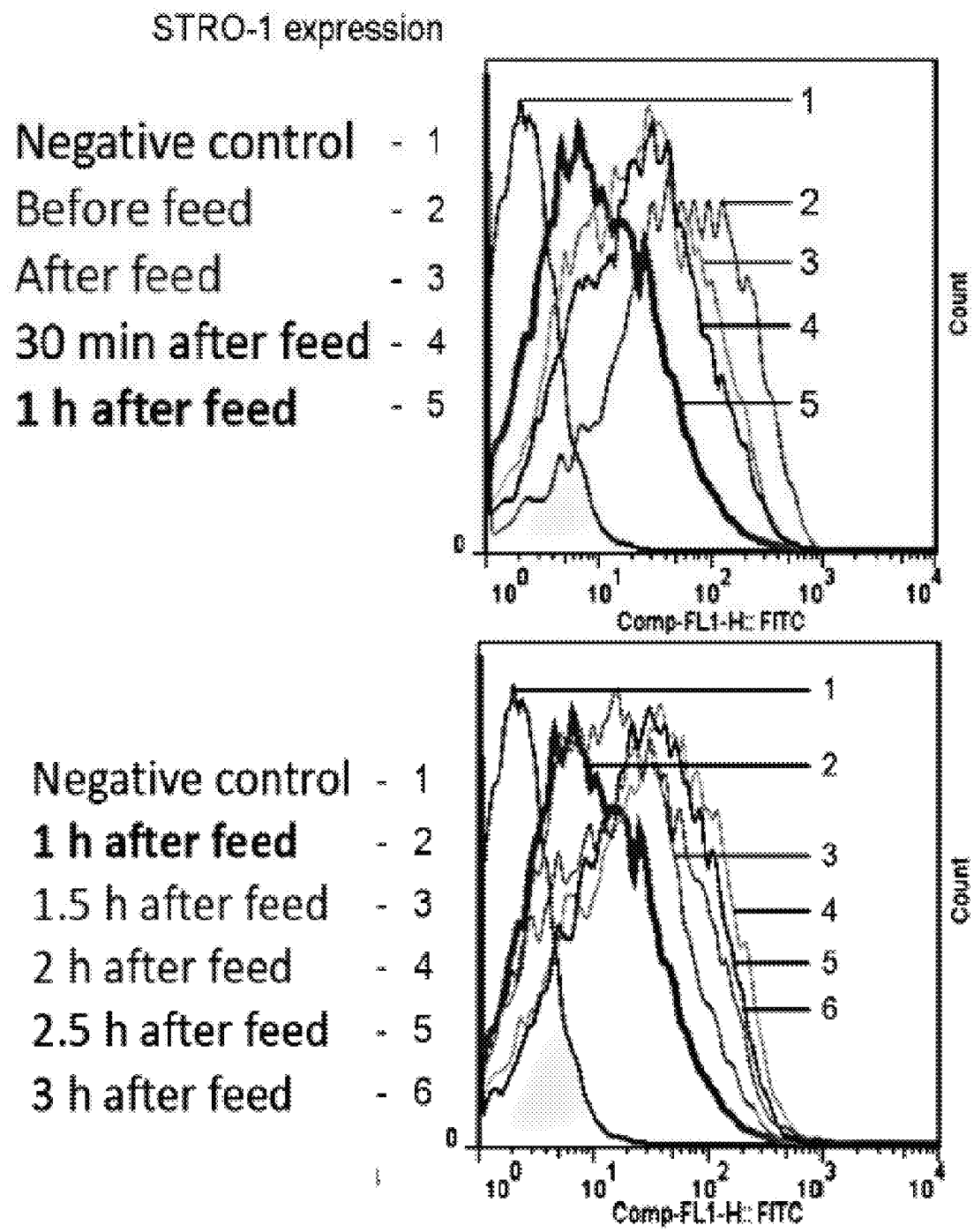
FIG. 2A shows that expression of the mesenchymal stem cell marker STRO-1 decreases after feeding.
Figure 2B:
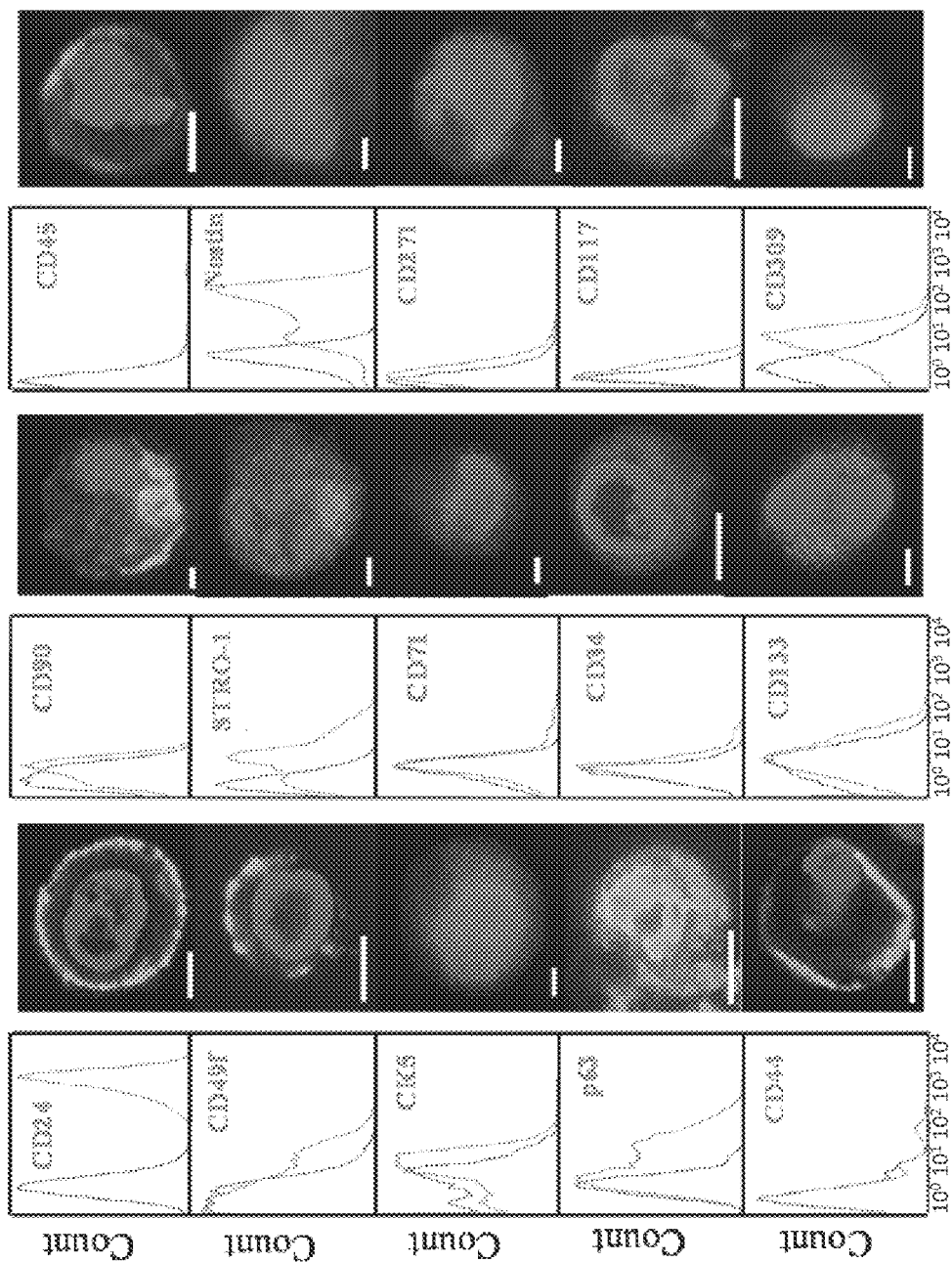
FIG. 2B provides representative flow cytometry profiles and positively-labeled fluorescent cell images for a number of cell markers in breastmilk, including CD24, CD90, CD45, CD49f, STRO-1, Nestin, CK5, CD71, CD271, p63, CD34, CD117, CD44, CD133 and CD309. Cell nuclei were stained with 4',6-diamidino-2-phenylindole (DAPI) in all images showing nuclear staining. Additional information on the antibodies used to detect the cell markers can be found in Table 1. Flow cytometry profiles are shown in comparison to a respective negative isotype control (human fibroblasts).

Further, characterisation of breastmilk cells by flow cytometry indicates that a change in cell composition also occurs after feeding. FIG. 2A shows that expression of the mesenchymal stem cell marker STRO-1 decreases following feeding with a minimum of STRO-1 positive cells seen at about 1 hour following feeding. In FIG. 2B an array of cells from breastmilk staining positive for a number of further cell markers, including CD24, CD90, CD45, CD49f, STRO-1, Nestin, CK5, CD71, CD271, p63, CD34, CD117, CD44, CD133 and CD309, together with a respective flow cytometry profile indicating the prevalence of such cells in comparison to a respective negative isotype control are shown. Further, as seen in FIG. 2C the presence of these markers could also be shown by immunohistochemistry staining of breastmilk cells.

Analysis of Differentiation Potential of the Lactating Breast

Figure 3:
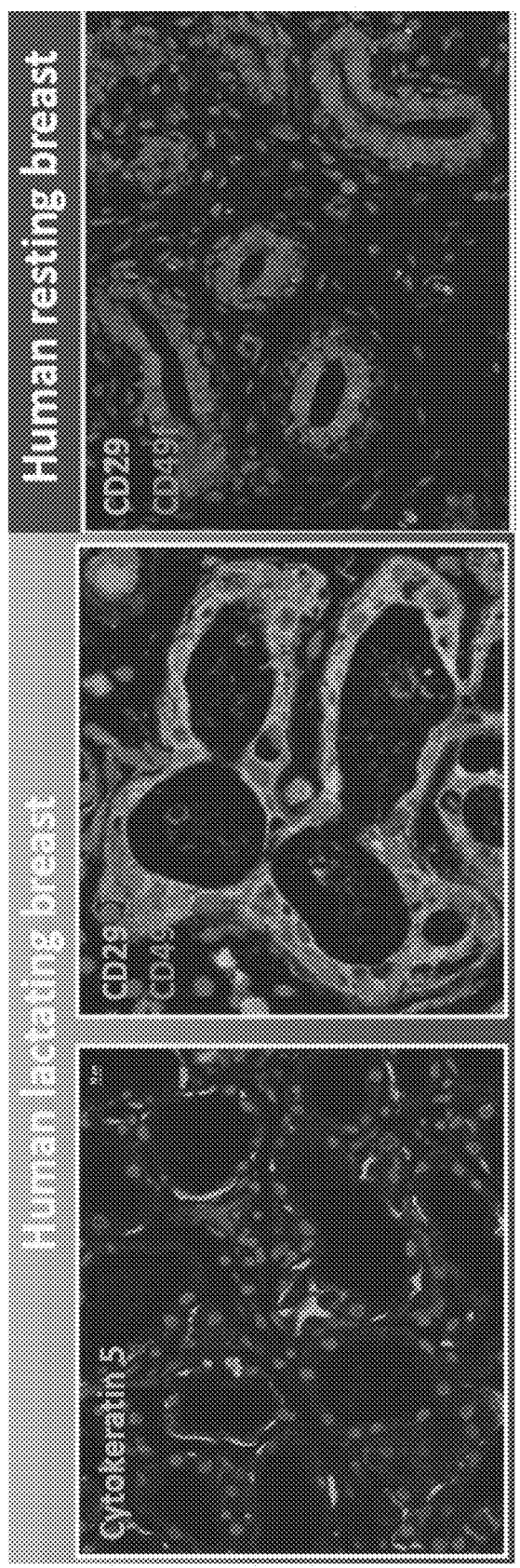
FIG. 3 shows representative cells for comparative cell marker immunofluorescence staining for lactating as well as resting breast tissue. Positive staining for cytokeratin 5, CD29 as well as CD49f (mammary stem cell markers) (see Table 1) was observed in tissue from lactating breasts whereas only a minimal signal for these markers was obtained in resting breast tissue. Cell nuclei were stained with DAPI.

As indicated above, when analysing tissue samples from resting as well as lactating breasts a clear difference was observed. For example, and referring to FIG. 3, positive in situ staining for Cytokeratin 5, CD29 as well as CD49f (mammary stem cell markers) was observed in tissue from lactating breasts whereas only a minimal signal for these markers was obtained in resting breast tissue.

Human Breastmilk Stem Cells Express hESC Markers

Figure 4A:
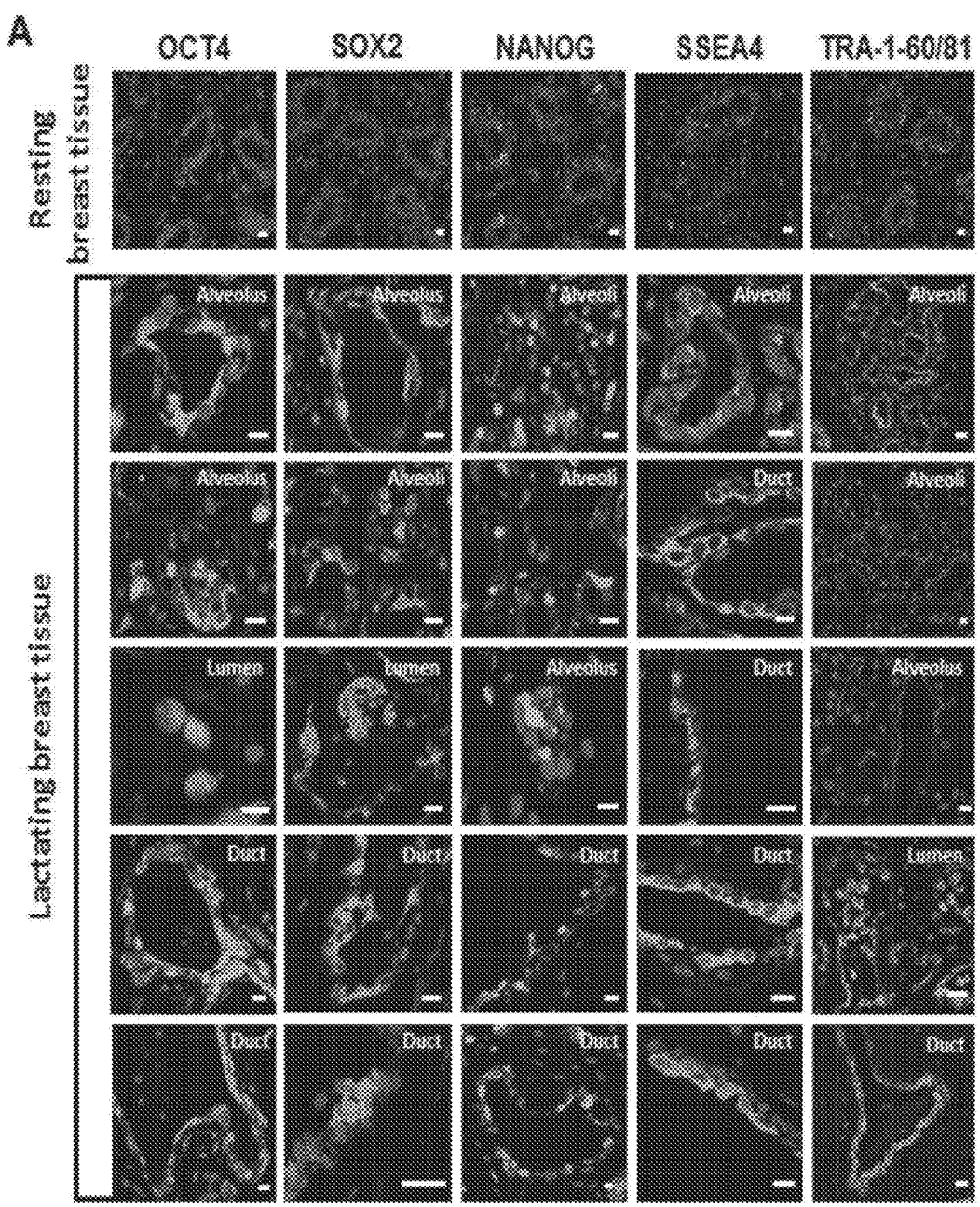
FIG. 4A depicts representative images of the embryonic stem cell marker expression detected in the luminal and basal epithelial layers in the alveoli and ducts of the mammary tissues. Normal resting and lactating human breast tissue biopsies were examined using immunostaining for expression of genes that affect self-renewal in embryonic stem cells, including Oct4, Sox2, Nanog, SSEA4 and Tra-1-60/Tra-1-81. (See Table 1).

When examining the molecular determinants of self-renewal and indicators of plasticity in MaSCs in the human, normal human resting and lactating breast tissue biopsies were also examined immunohistochemically for expression of genes that constitute the core circuitry of self-renewal in hESCs. No or minimal expression of Oct4, Sox2, Nanog, SSEA4 and Tra-1-60/Tra-1-81 were observed in resting mammary tissues (FIG. 4A). By contrast, a clear upregulation of ESC genes was observed in normal lactating mammary tissues, where distinct patterns of gene expression were recorded (FIG. 4A). The transcription factors (TFs) Oct4, Sox2 and Nanog were expressed both in the luminal and the basal epithelial layers in the alveoli and ducts of the lactating epithelium (FIG. 4A). Differences were observed in the distribution and level of ESC gene expression between different ducts and alveolar batches, confirming a previously reported developmental heterogeneity between different epithelial compartments within the same tissue (Molenaar et al. 1992). Moreover, even within a duct or alveolus expression differences were evident, ranging from absence of expression, minimal cytoplasmic expression, clear nuclear expression, and mixed cytoplasmic and nuclear expression within a cell (FIG. 4A). For all three TFs, the highest expression level was observed in the myoepithelial layer compared to the luminal layer both in ducts and alveoli. SSEA4 was more irregularly expressed in both ducts and alveoli (FIG. 4A). Tra-1-60 and Tra-1-81 were restricted to the luminal cell surface in alveoli, but were more irregularly expressed in ducts. Co-expression of these markers was observed in cell subpopulations in the ductal and alveolar zones. Positive cells were also captured in the lumen of ducts and alveoli (FIG. 4A), suggesting their presence in breastmilk.

Figure 4B:
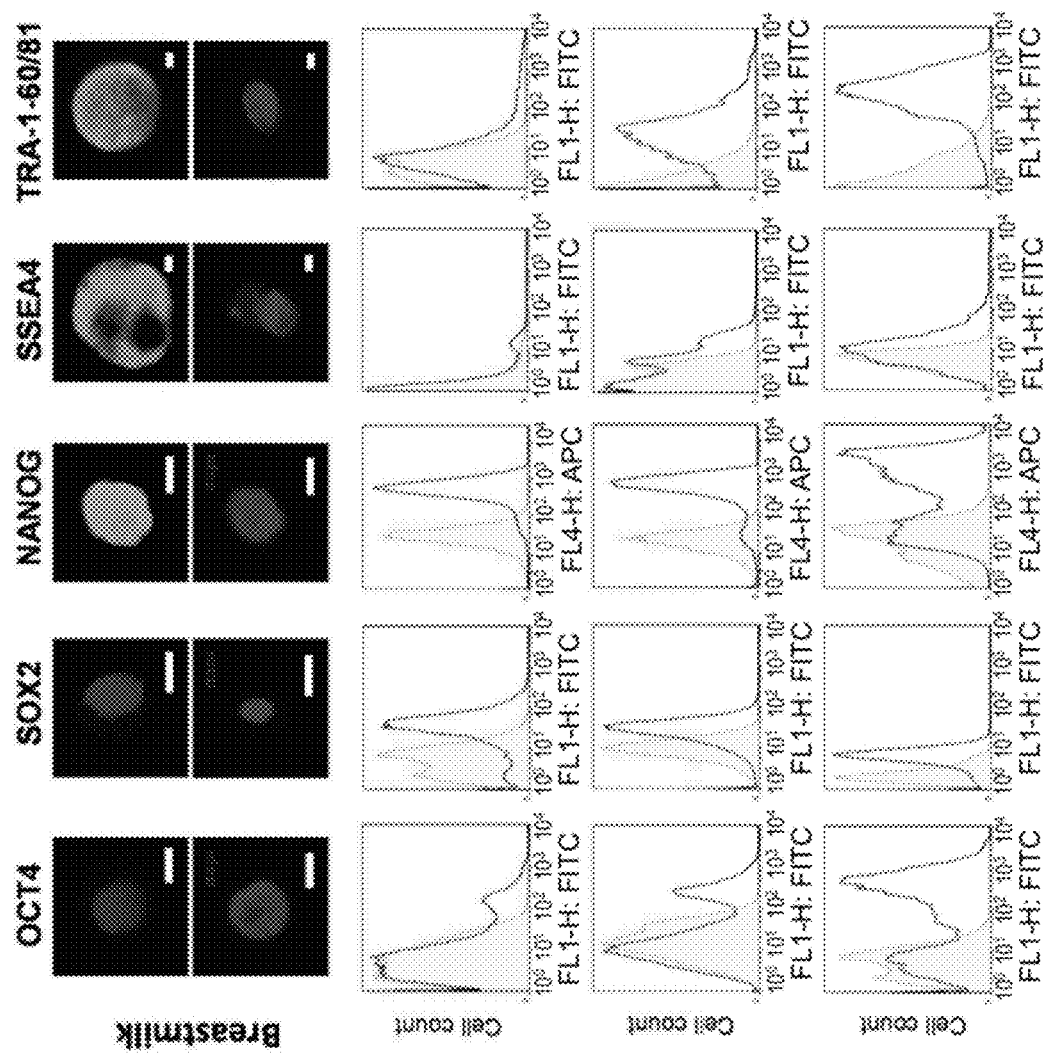
FIG. 4B depicts the detection of the Oct4, Sox2, Nanog, SSEA4 and Tra-1-60/Tra-1-81 in isolated cells from freshly expressed breastmilk samples. Proteins were detected using immunofluorescence staining using the cell marker antibody listed in Table 1. Cell nuclei were stained with DAPI. Fluorescence-Activated Cell Sorting (FACS) was also used. An analytic gating strategy was developed for the quantification of protein expression by FACS, which excluded interference by dead cells and/or fat globules. Expression levels obtained with FACS were analyzed as the percentage of positive cells and as the standardized difference in mean fluorescence intensity (MFI) between the control cells (human fibroblasts) and the test. Representative counts are shown in FIG. 4B.
Figure 4C:
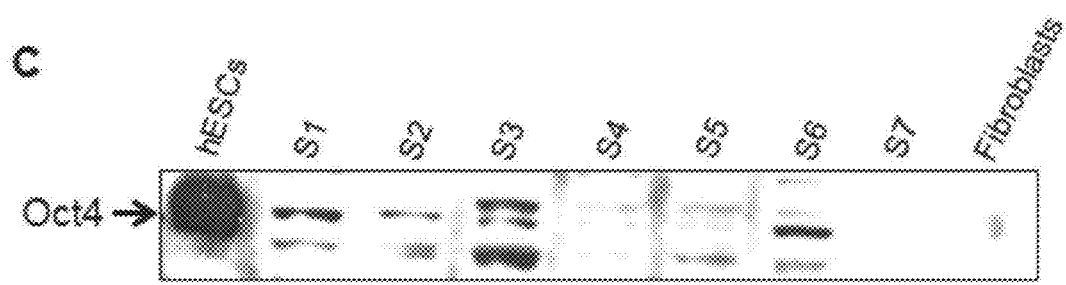
FIG. 4C shows Oct4 protein expression in several breastmilk samples (noted as S1, S2, S3, etc.) using western blot. Human fibroblasts were used as a negative control, while hESCs were used as a positive control.
Figure 4D:
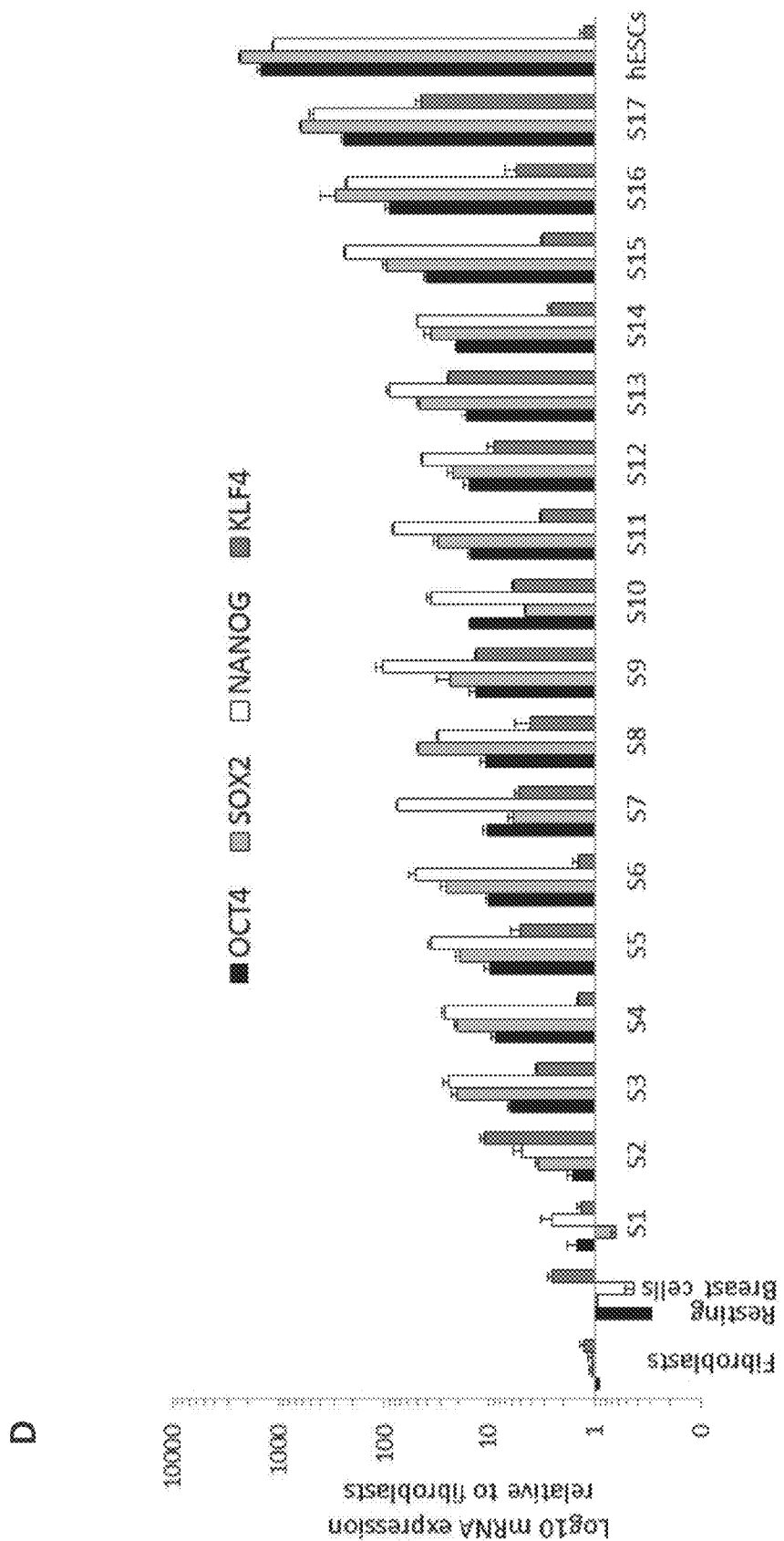
FIG. 4D shows the quantity of mRNA for Oct4, Sox2, Nanog, and KLF4 in several breastmilk samples using quantitative RT-PCR, as further detailed below.

To non-invasively access this enriched ES-marker+ cell population from the lactating breast, freshly expressed breastmilk donated from women from various lactating stages (month 1 to year 5 and beyond, n>70) was used. Total cells were isolated from the freshly expressed breastmilk samples and examined for ex vivo expression of ESC markers at the protein and mRNA levels, using immunofluorescence staining (IF) (FIG. 4B), Fluorescence-Activated Cell Sorting (FACS) (FIG. 4B), Western Blotting (WB) (FIG. 4C) and RT-PCR (FIG. 4D). All antibodies and probes were first standardized using human fibroblasts as negative control. A clear nuclear, and sometimes perinuclear localization of Oct4, Sox2 and Nanog was observed using IF in breastmilk cell subpopulations, whereas SSEA4 and Tra-1-60/Tra-1-81 were localized on the cell surface (FIG. 4B). An analytic gating strategy was developed for the quantification of protein expression by FACS, which excluded interference by dead cells and/or fat globules. Expression levels obtained with FACS were analyzed as the percentage of positive cells and as the standardized difference in mean fluorescence intensity (MFI) between the control and the test. A wide variation in FACS expression levels was observed among the breastmilk cell preparations examined, ranging from 4-96% of total cells for Oct4, Sox2 and Nanog, and 0.1-93% for the surface antigens SSEA4 and Tra-1-60/Tra-1-81. Among these genes, Nanog and Tra-1-60/Tra-1-81 were the most highly expressed, followed by OCT4. Co-expression of these genes by single cells was demonstrated both with IF and FACS. WB confirmed ESC gene expression at the protein level (FIG. 4C). Similar to protein expression, a wide variation was observed in mRNA expression levels among samples from different women (FIG. 4D). Oct4, Sox2 and Nanog mRNA expressions were lower in hBSCs compared to the hESC line H7, but significantly higher than that of human fibroblasts and cells derived from resting breast mammoplasties (p=<0.0001; FIG. 4D). Among the breastmilk samples analysed, the highest level of ESC gene mRNA expression was observed in a participant who was breastfeeding and was concurrently pregnant with her next child. hBSCs expressed Nanog mRNA at higher levels compared to Oct4 and Sox2, which was consistent with the results obtained using IF and FACS for protein expression. Interestingly, Klf4 expression by hBSCs was significantly higher than that of hESCs (p=<0.0001; FIG. 4D). In addition to the above ESC markers, hBSCs expressed Rex1, hTERT and GDF3. The above findings established expression of ESC genes at the protein and mRNA levels by hBSCs.

Clonogeneicity and Self-Renewal of Breastmilk Stem Cells

Figure 5A:
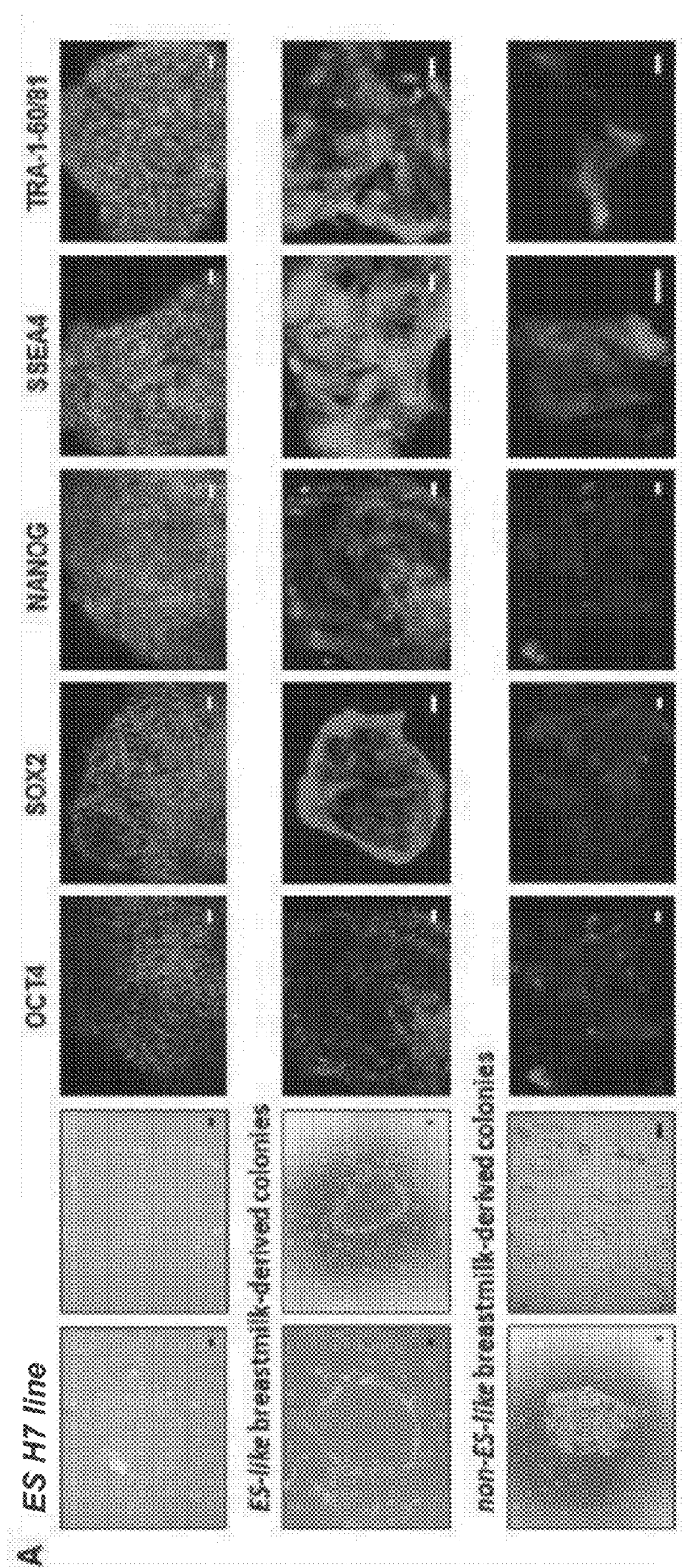
FIG. 5A illustrates the morphology of hBSCs and the expression profile of typical ESC markers Oct4, Sox2, Nanog, SSEA4, SSEA3, and Tra-1-60/Tra-1-81 in embryonic stem cell-like colonies derived and specifically expanded in spheroid culture. Cells from breastmilk-derived colonies that did not show ES-like morphology showed reduced ESC marker fluorescence. Positive control cells (ES H7 line) are shown. Additional information on the cell marker detection can be found in Table 1.

A distinguishing property of hESCs is the formation of flat, compact and encapsulated colonies in feeder culture conditions in hESC medium. These colonies typically express the pluripotency genes Oct4, Sox2, Nanog, SSEA4 and Tra-1-60/Tra-1-81 (FIG. 5A). To examine the clonogeneicity, morphology and phenotype of hBSCs in the presence of feeders and compare it with that of hESCs, cells isolated from freshly expressed breastmilk were cultured in the presence of feeders in hESC medium. A rapid cellular proliferation was first observed in suspension, during which individual cells divided and formed spherical structures. Although expansion in suspension continued, within 4-7 days of plating adherent individual cells and colonies appeared. The suspension cells were removed with the first media change and the adherent colonies were allowed to expand. Two distinct types of adherent colonies were observed: ES-like flat, compact encapsulated colonies with high nucleus:cytoplasm ratio, and non-ES-like colonies (FIG. 5A). The non-ES-like colonies had various morphologies, from a mesenchymal-like to an epithelial-like or mixed morphology (FIG. 5A). The formation frequency of the two colony types differed between different breastmilk samples, with 68-100% (mean 90±3%, n=11) of all colonies displaying the ES-like morphology. In the breastmilk samples tested, the frequency of ES-like colony forming cells ranged from 1 in 15,000 to 1 in 1,750,000 (n=11).

All ES-like hBSC colonies expressed Oct4, Sox2, Nanog, SSEA4, SSEA3, and Tra-1-60/Tra-1-81, with the TFs being localised primarily in the nucleus (FIG. 5A). Similarly to hESCs, spontaneous differentiation in the centre of the ES-like colonies was occasionally observed, particularly when they were allowed to expand for more than 2 weeks. Most non-ES-like colonies expressed these genes at very low levels, if at all. Based on TF gene expression, three distinct cell types were observed within the non-ES-like colonies: negative cells, dimly positive cells with TF expression primarily in the cytoplasm, and few smaller round weakly attached cells that were clearly positive in the nucleus (FIG. 5A). SSEA4 and Tra-1-60/Tra-1-81 were expressed at higher levels than the TFs in the non-ES-like colonies, but at lower levels than in the ES-like colonies. It must be noted that in addition to colonies obtained, single attached cells that failed to expand in 2D were also observed. Many of these cells expressed ESC genes at high levels. The nature and properties of these cells remains to be established.

ES-like colonies were passaged in secondary feeder cultures, where they generated identical colonies with ES-like morphology and phenotype. Similar colony formation characteristics were observed when breastmilk cells were cultured in the absence of feeders in gelatine-coated or uncoated adhesion plates, although attachment and colony formation success was higher in the presence of feeders. These data suggest that a subpopulation of hBSCs possesses ES-like features, clonogeneicity and self-renewal properties.

3D Culture Enriches for hESC Gene Expression in Breastmilk Stem Cells

Figure 5B:
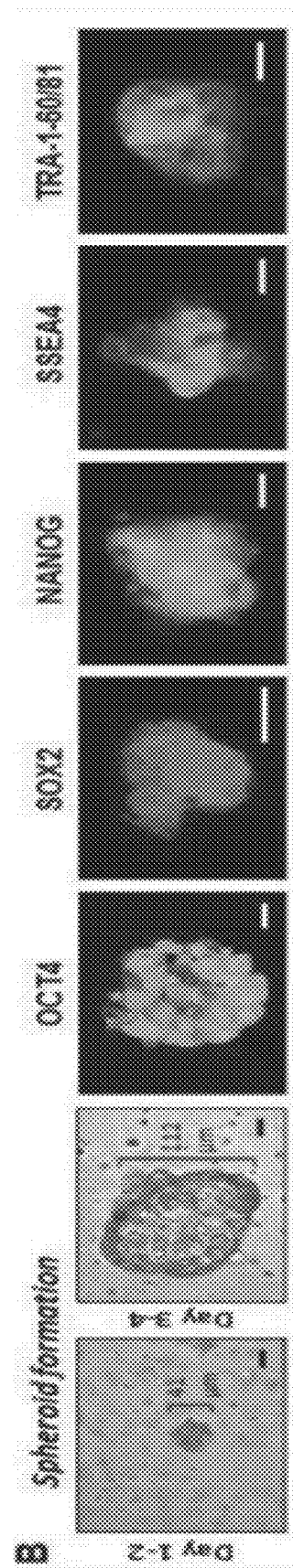
FIG. 5B shows breastmilk-derived spheroids as observed by cell morphology and immunofluorescence for ESC markers. Co-expression of several ESC marker genes were observed, and cell nuclei were stained with DAPI.

As a propensity for initial expansion of hBSCs in suspension via spheroid formation (even in adhesion plates) was observed, the characteristics of breastmilk cells when cultured in 3D in ultra-low binding plates were examined. With or without the presence of extracellular matrix (Matrigel), breastmilk cells rapidly formed spheroids, which could be successfully maintained through several passages (FIG. 5B). Typically, the most rapid increase in spheroid size was observed within the first 1-4 days (FIG. 5B). The ability of spheroid formation, spheroid sizes and size increase in the course of culture varied between different breastmilk samples, with smaller magnitude variations observed also between spheroids of the same sample. ESC gene expression in breastmilk-derived spheroids was confirmed by IF (FIG. 5B), which revealed co-expression of these genes, and RT-PCR (FIG. 5B).

Interestingly, a significant upregulation of ESC genes was observed during spheroid formation that equalled or sometimes exceeded the expression levels of hESCs. A time-course analysis of Oct4, Sox2 and Nanog mRNA expression from day 1 to day 12 of spheroid formation revealed a stable upregulation of these genes, which typically peaked after day 7, such as day 9, and reached or exceeded the expression levels of hESCs (FIG. 5B). Of note, variations in the extent of upregulation of ESC genes and the day which expression levels peaked were observed among different breastmilk samples. Therefore, culture of breastmilk cells in suspension provides a rapid method for expansion of the hBSC population with ES-like features.

Determination of the Differentiation Potential of BSCs—Spontaneous and Directed Differentiation of Breastmilk Stem Cells into Cells Originating from all Three Germ Layers To determine the differentiation potential of the identified ESC-like hBSCs spontaneous as well as directed differentiation was assessed. In hESCs and hiPSCs (human induced pluripotent stem cells), an initial 3D embryoid body formation and subsequent cultivation of the embryoid bodies in adherent conditions results in spontaneous differentiation into cells from all three germ layers (Itskovitz-Eldor et al., 2000; Takahashi et al., 2007). Therefore, breastmilk cells were allowed to form 3D spheroids. By day 4-7, some cells had attached. The remaining spheroids were then transferred into new wells where adherent cells appeared in 1-2 days. Both the initial and subsequent adherent cells were cultured for another 2-3 weeks. The resultant cultures contained a mixture of adherent cells/cell colonies with various morphologies, including those of epithelial cells, mesenchymal cells, neural cells, and cobblestone-like cells (which stained positive for corresponding markers), indicating that spontaneous differentiation had occurred.

Figure 6A:
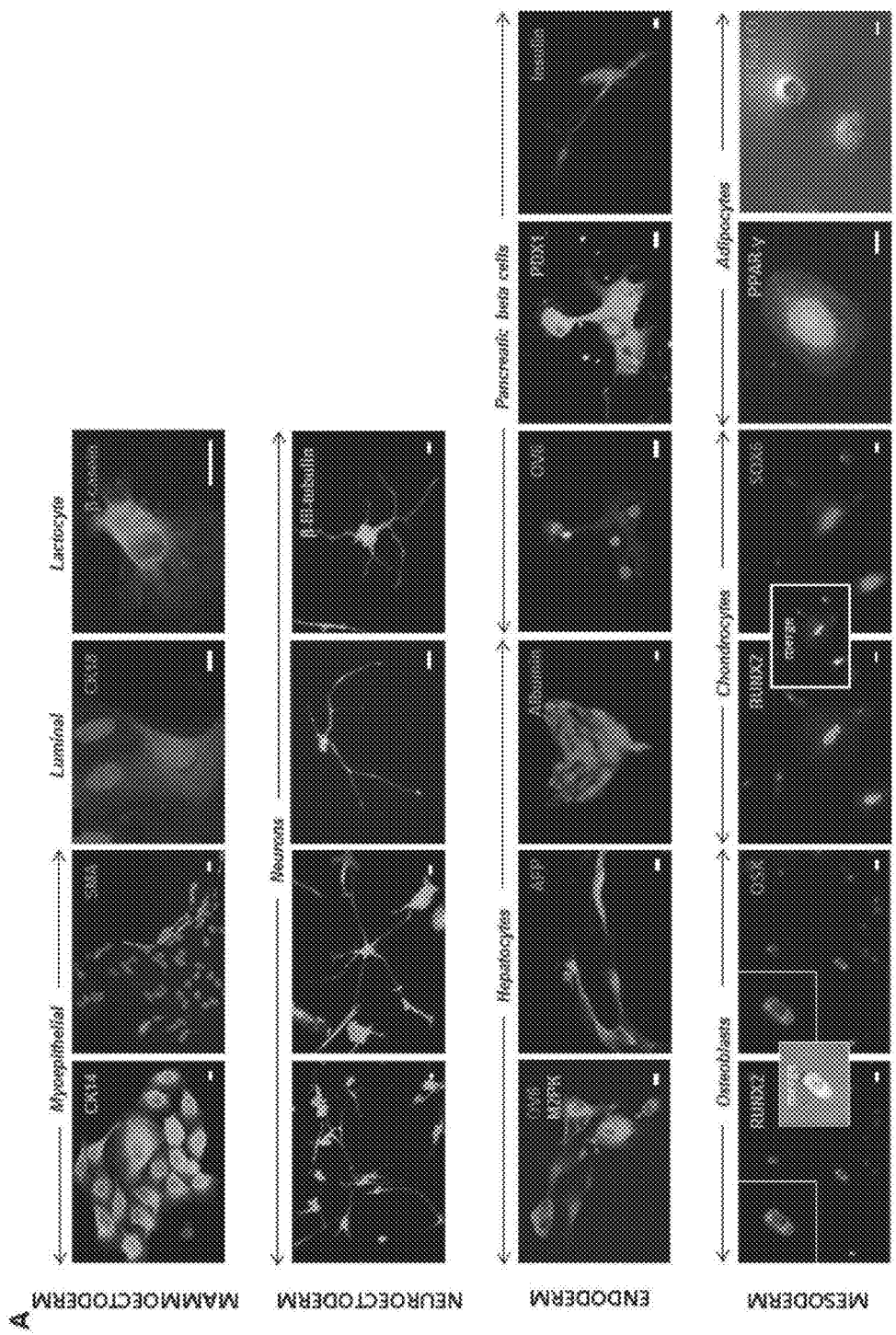
FIG. 6A depicts immunofluorescent detection of various markers of differentiated cells after growing hBSCs under particular culture conditions, and illustrates the differentiation potential of spheroid-expanded hBSCs. Example markers for myoepithelial cells (CK14$^+$, SMA$^+$), neurological cells (nestin, β-III-tubulin), glial cell markers (glial fibrillary acidic protein (GFAP), S100 protein), osteoblasts (Runx2, OSX), chondrocytes (Runx2$^+$/Sox-6$^+$), adipose cells (Oil Red O$^+$, PPAR-γ), endodermal cells (OV-6), hepatocytes (albumin, α-fetoprotein (AFP), M2 isoenzyme of pyruvate kinase (M2PK)), pancreatic cells (PDX1, insulin). Further details on the detection of these and other markers can be found in Table 1. Cell nuclei were stained with DAPI if applicable.
Figure 6B:
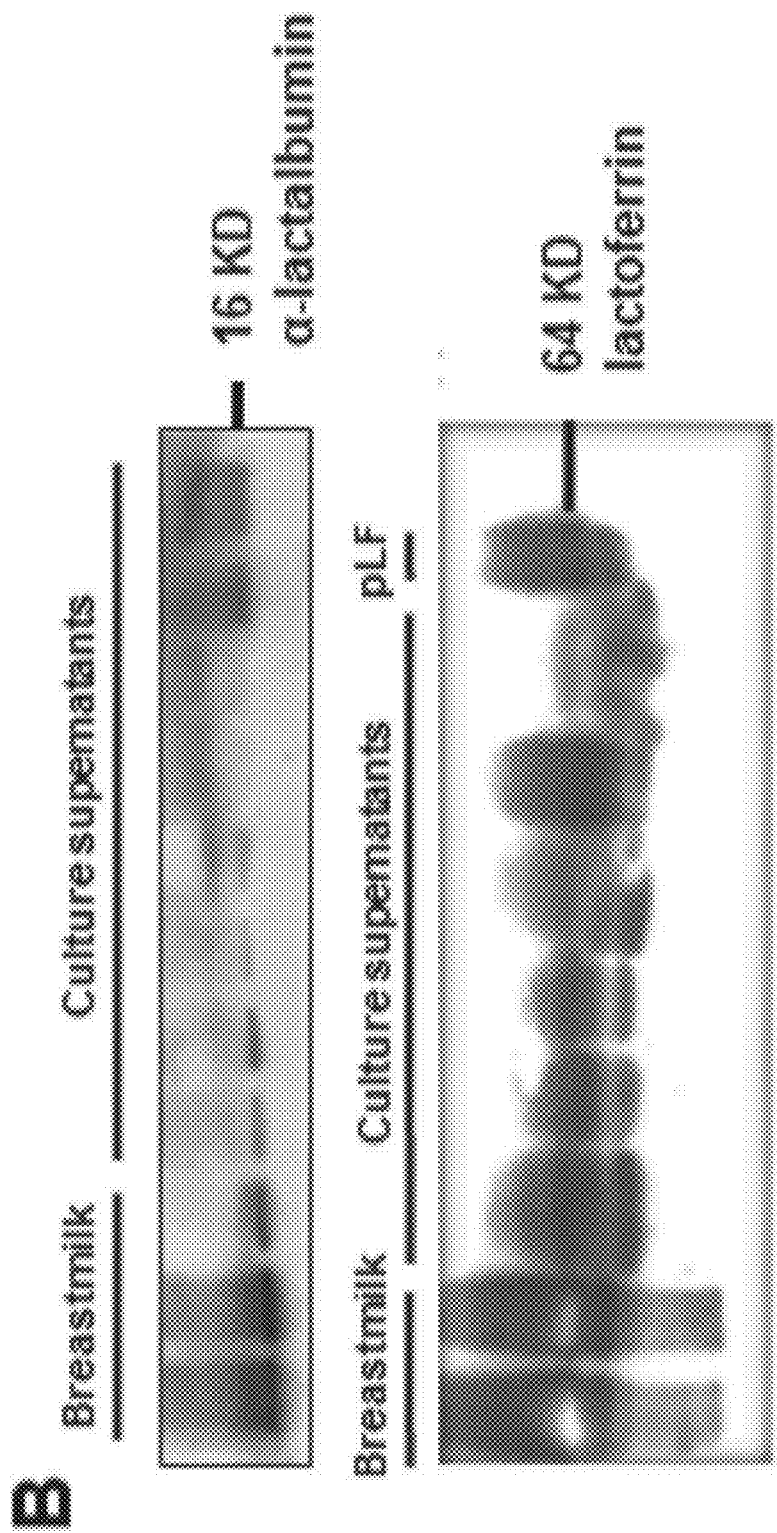
FIG. 6B depicts a Western blot showing luminal cells (CK18$^+$/CD49f$^-$) that spontaneously synthesised several milk proteins including β-casein, lactoferrin, and α-lactalbumin at week 3.
Figure 6C:
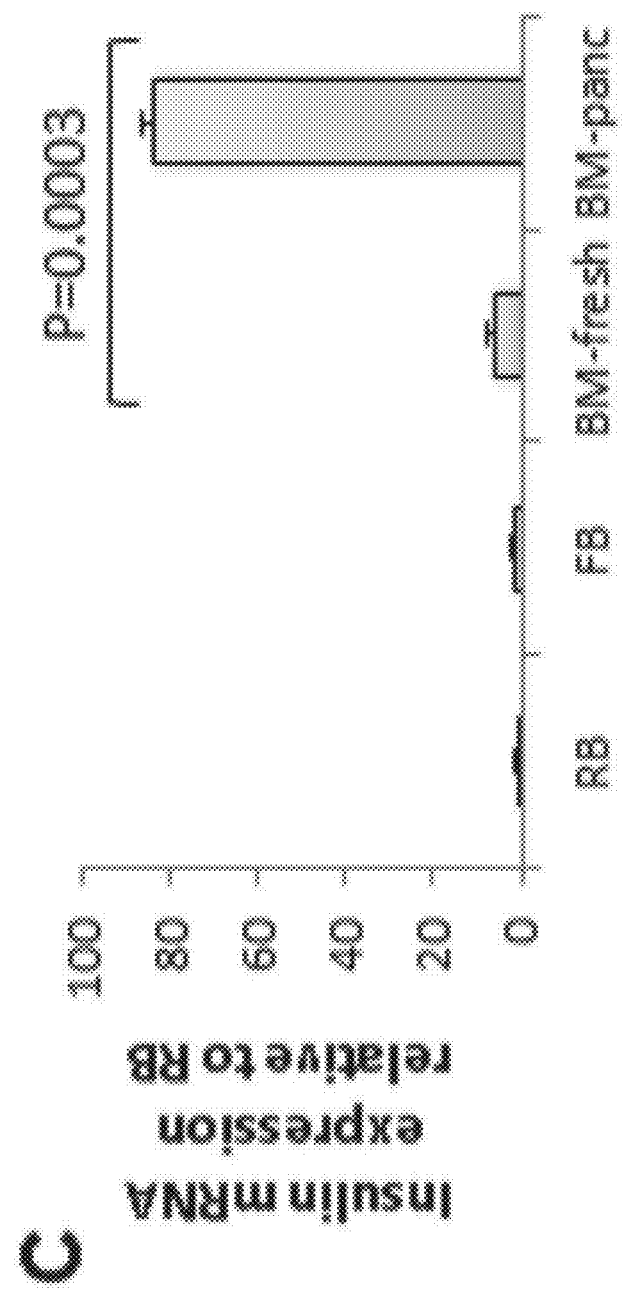
FIG. 6C shows the results of RT-PCR indicating that hBSC cells cultured under pancreatic conditions produce significantly higher amounts of insulin mRNA than freshly isolated hBSC cells and control cells.
Figure 7:
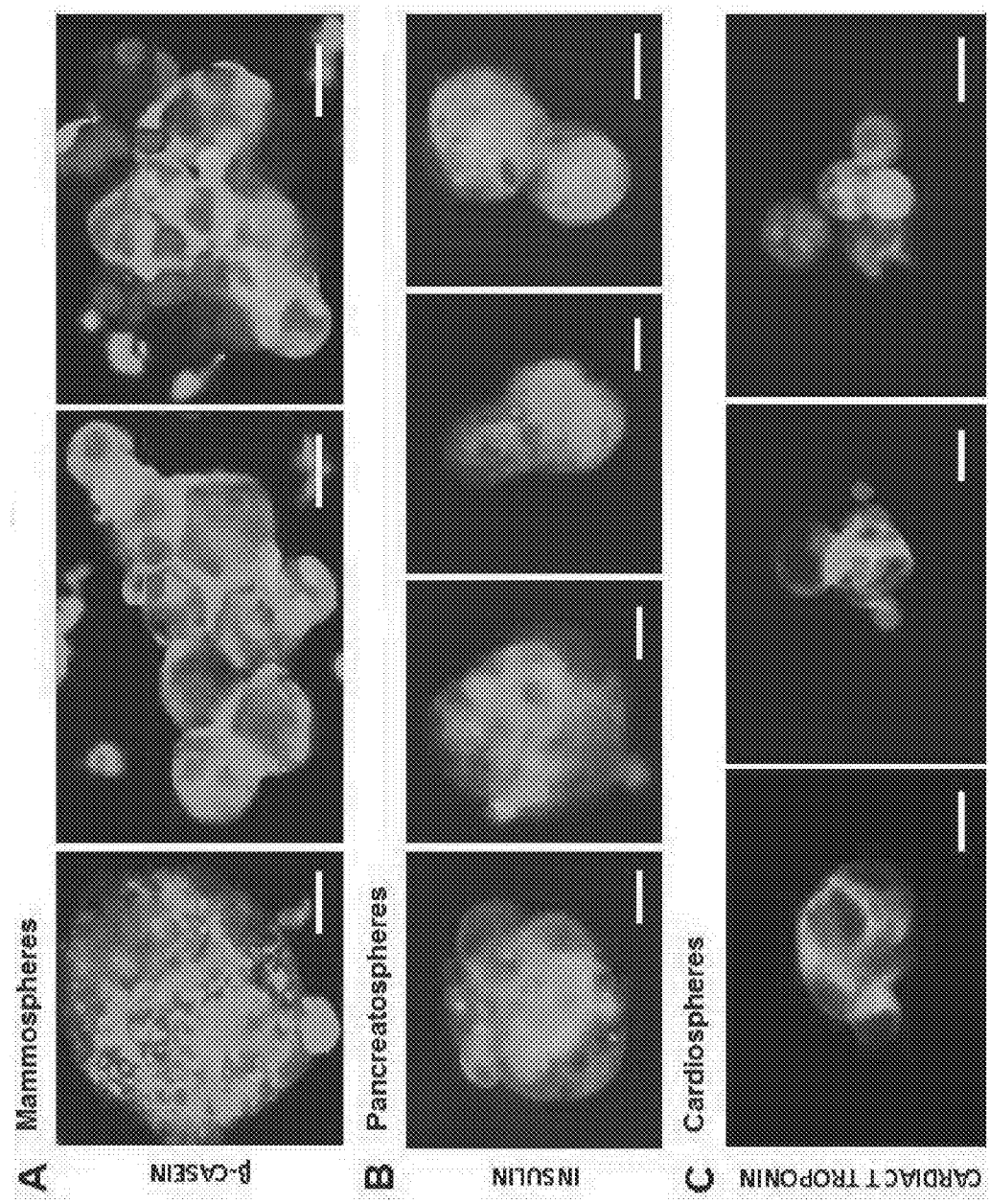
FIG. 7 depicts representative immunological fluorescent staining of cell-type specific markers in hBSCs subjected to directed differentiation in spheroid culture. When hBSCs were cultured in the respective differentiation media, mammospheres producing milk proteins (β-casein), pancreatospheres expressing insulin, and cardiospheres expressing cardiac T troponin were all obtained within 3-4 weeks of first culturing. Cell nuclei were stained with DAPI.

Further, lineage-directed differentiation of hBSCs under 2D culture conditions, i.e. in specific growth media using methods previously reported for hESCs, was examined. Initially, the potential of differentiation into the two mammary lineages was confirmed. Within the first 2 weeks of culture in mammary differentiation conditions, myoepithelial cells (CK14$^+$, SMA$^+$) were observed in the attached colonies (FIG. 6A). On week 3, luminal cells (CK18$^+$/CD49f$^-$) were detected, some of which spontaneously synthesised milk proteins (β-casein, lactoferrin, α-lactalbumin; FIG. 6B) and breastmilk characteristic oligosaccharides, which were secreted and detected in the culture supernatant. Under neurogenic conditions, cells with neuronal morphology and expression of nestin and β-III-tubulin were detected within 2-3 weeks of culture (FIG. 6A) as well as cells expressing glial cell markers such as glial fibrillary acidic protein (GFAP) and S100 protein. Under osteoblastic conditions, cells with nuclear expression of Runx2, a transcription factor essential for osteoblastic differentiation (FIG. 6A) was detected. Some Runx2$^+$ cells co-expressed OSX, an osteoblast-specific transcription factor required for bone formation. Under chondrogenic conditions, cells with the chondrocyte marker profile (Runx2$^+$/Sox-6$^+$) were identified after 2-3 weeks of culture (FIG. 6A). Under conditions promoting adipogenic differentiation, cells with lipid droplets (Oil Red O$^+$) positive for the adipogenic transcription factor PPAR-γ were observed (FIG. 6A). Differentiation towards endodermal cells was examined. Breastmilk cells cultured in hepatocyte differentiation conditions initially upregulated the endodermal progenitor marker OV-6, which was subsequently downregulated with concurrent upregulation of the mature hepatocyte markers α-fetoprotein and M2 isoenzyme of pyruvate kinase, and the functional hepatocyte marker albumin (FIG. 6A). Under pancreatic differentiation conditions, upregulation of the mature beta cell marker PDX1 was observed, and expression of insulin in the resulting cells was confirmed by IF (FIG. 6B) and RT-PCR (FIG. 6C). Directed differentiation in 3D conditions was also examined by growing breastmilk-derived spheroids in differentiation media for a longer period. Indeed, in corresponding media, mammospheres producing milk proteins (β-casein), pancreatospheres expressing insulin, and cardiospheres expressing cardiac T troponin were obtained within 3-4 weeks of culture (FIG. 7). In all differentiation inductions, upregulation of the differentiation genes was accompanied by downregulation of ESC genes.

Teratoma Assay of Breastmilk-Derived MaSCs

One assay to establish the in vivo pluripotency of a cell population is to test whether the cells have the ability to induce teratoma formation. However, at the same time, tumorigenicity, i.e. the potential of cells to form a teratoma/tumor, is a key concern in the practical application of stem cell therapies. For example, the formation of tumors, such as teratomas, following transplantation of hESC-derived precursor cells has been observed in a number studies (Roy et al., 2006; Erdo et al., 2003; Hedlund et al., 2007; Pruszak et al., 2007; Björklund et al., 2002; Riess et al., 2007; and Aubry et al., 2008) and was also noted by Wernig et al., 2009 in a recent study in which iPS cell-derived neural precursors were transplanted into a 6-OHDA lesion model of Parkinson's disease. The formation of teratomas is thought to result from a proportion of the transplanted cells retaining an undifferentiated state and having tumorigenic potential. Accordingly, teratoma formation following transplantation of hESC- or iPS cell-derived precursor cells presents a major obstacle for the clinical application of stem cell therapy, as tumor formation as a clinical result of cell transplantation therapy in human patients is unacceptable.

To establish whether hBSCs are capable of forming teratomas when injected subcutaneously into dorsal flanks of immunodeficient (SCID) mice, 15 mice were injected with freshly isolated total breastmilk cells ($3 \times 10^6$-$32 \times 10^6$) or with spheroid-derived breastmilk cells ($2 \times 10^5$-$10^7$). Nine weeks after injection, mice were examined and no tumor formation was observed, suggesting that hBSCs do not form tumors under the conditions employed. By contrast, positive control animals injected with as few as 50 cells of p86-OTBC-L1 (OCT4-tranduced breast cancer cells) showed formation of poorly differentiated tumors (Beltran et al., 2011).

Discussion

A stem cell population with ES-like properties and multilineage differentiation potential has been identified in the human lactating breast and breastmilk. This cell population is scarce in the normal resting breast tissue, suggesting (a) that at least some of these cells may be mobilised from other tissues during lactation, and/or (b) that it is remnant from embryonic development in the resting breast, where it is scarce and in a quiescent state. Pregnancy- and lactation-associated hormonal cues activate this cell population via stimulation of a self-renewal program mediated by a marked upregulation of embryonic stem (ES) cell genes. This newly described cell population was non-invasively accessed via freshly expressed breastmilk and ex vivo, in situ and in vitro characterisation of these cells was performed.

Breastmilk contains a heterogeneous cell population, which reflects the cellular hierarchy of the lactating mammary epithelium. Both in lactating breast tissues and breastmilk samples examined a high, yet variable, percentage of cells expressing the ESC pluripotency transcription factors Oct4, Sox2, Nanog, Klf4, SSEA4, Tra-1-60/Tra-1-81 was observed. Nevertheless, the differing subcellular localisation (from cytoplasmic to nuclear) and levels of expression between different cells further reinforce the presence of a cellular hierarchy, from early-stage stem cells to committed progenitors, and stages in between. Although all these cells express pluripotency genes at some level, it is proposed that not all are at the same developmental stage and not all have the same self-renewal and differentiation potential. For example, a much lower frequency of ES-like colony formation by breastmilk-derived cells in feeder culture was observed and, moreover, in these cultures a large number of single, attached cells was observed, which did not proliferate, yet expressed ESC genes at high levels. This is in accordance with the initial high ESC gene expression levels seen pre-plating in the freshly isolated breastmilk cell population. In addition to the single attached cells and ES-like colonies, non-ES-like colonies were observed in feeder cultures, which retained some expression of ESC genes, but at much lower levels compared to ES-like colonies. The non-ES-like colonies displayed varying morphologies, from epithelial to mesenchymal to mixed. Based on the above, it is hypothesized that the non-ES-like colonies originate from the expansion of more committed luminal or myoepithelial or common progenitors present in breastmilk, suggesting that ESC genes are not completely downregulated in the more committed mammary progenitor cells.

Figure 5C:
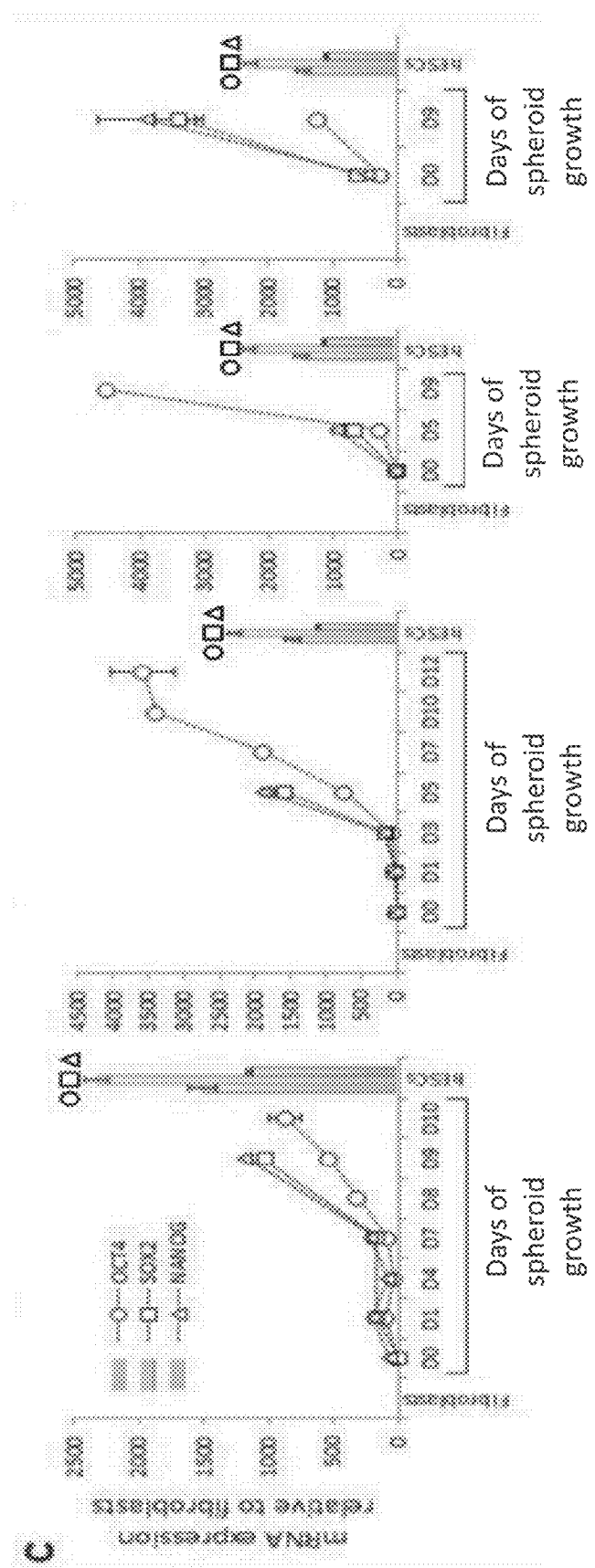
FIG. 5C shows RT-PCR quantification of mRNA levels for Oct4, Sox2, and Nanog at various time points during spheroid formation. Negative controls (fibroblasts) and positive controls (hESC) are also shown.

It therefore becomes clear that a wide spectrum of developmental stages and functionalities is represented in breastmilk. Amongst the more committed progenitor and differentiated cells, breastmilk contains a stem cell population, which is similar to hESCs, yet not identical. Freshly isolated breastmilk cells expressed the core TF network governing pluripotency in hESCs (Young, 2011). Interestingly, of the three TFs (Oct4, Sox2 and Nanog), Nanog was expressed at higher levels among the breastmilk samples tested. Nanog is the key self-renewal regulator essential for early development and for maintaining the ground-state pluripotency of ESCs (Ding et al., 2012). Expression levels of ESC genes in freshly isolated breastmilk cell preparations were lower than in hESCs, likely due to the cellular heterogeneicity of breastmilk. However, 3D culture conditions enriched for the ES-like hBSCs in a time-dependent manner, with expression levels of ESC genes that equalled or exceeded those of hESCs. Since spheroid formation conditions are thought to better represent the in vivo environment (Lee et al., 2007), it is postulated that ESC gene expression levels in the breastmilk-derived spheroids may reflect those of the ES-like cell population present in the lactating breast epithelium. The propensity of breastmilk cells to grow in suspension rather than as adherent cells is indicative of a migratory character, another similarity with hESCs cells. Furthermore, the findings are in accordance with previous studies reporting increased expression of OCT4 during spheroid culture of breast cancer cell lines (Wang et al., 2010) and of epithelial cells derived from resting breast tissue mammoplasties (Blancafort, unpublished data). However, the increase in OCT4 expression during spheroid culture in both breast cancer cell lines and normal epithelial cells from resting breast tissue is in the order of 3-5 times, whereas in hBSCs in the order of hundreds to thousands of times, often reaching or exceeding the expression levels of hESCs (FIG. 5C). These findings support the pre-existence in the resting breast of a quiescent stem cell population which expands during pregnancy and lactation. As such, these findings provide a useful method for expansion of the ES-like hBSC population for future purposes. In addition, it suggests the possibility that some of these cells may have been mobilised from other tissues.

In addition to ESC gene expression, hBSCs formed ES-like colonies in feeders in hESC culture conditions, with morphology and phenotype that closely resembled that of hESCs. These hBSC-derived colonies could be serially passaged in secondary feeders and in 3D culture, demonstrating clonogeneicity and self-renewal. Furthermore, similarly to hESCs, hBSCs demonstrated spontaneous differentiation towards various cell types in vitro, and were capable of directed differentiation into cell types of mammary, neuroectodermal, mesodermal and endodermal origins. The resultant differentiation progressed to functional cells, including milk-secreting lactocytes, albumin-producing hepatocytes, and insulin-producing beta islet cells.

However, breastmilk cells injected subcutaneously in immunodeficient mice did not form tumors. hESCs and hiPCSs form teratoma-like masses when injected in immunodeficient mice, an assay that is used as an indicator of in vivo pluripotency (Lensch et al., 2007; Takahashi et al., 2007). Nevertheless, adult cells with pluripotent features and low tumorigenicity, i.e. that do not form teratomas when injected subcutaneously in mice, have been previously described, such as the very small ES-like cells (VSELs) isolated from the bone marrow and other adult tissues in mice (Ratajczak et al., 2011). Similarly to what has been previously suggested for the nature of VSELs, in the normal breast epigenetic modifications of the ES-like stem cells identified here may be responsible for maintaining them at a controlled state of self-renewal, prohibiting uncontrolled proliferation and tumor formation. It is proposed that the ESC TF network upregulated in the normal breast during lactation plays a fundamental role in the remodelling of the breast necessary to support its development towards a milk-secretory organ. Due to inherent expression of ESC TFs, these cells accessed via breastmilk are capable of multi-lineage differentiation in vitro. Importantly, disruption of this transcriptional network during pregnancy and lactation, failure to silence these genes during involution, or their aberrant upregulation in the resting breast may be at the core of malignant transformation in the breast. In accordance with this, it has been shown that forced ectopic expression of Oct4 in cells from the resting epithelium results in aberrant expansion of MaSCs possessing multi-lineage potential and displaying tumor-initiating features (Beltran et al., 2011). Future work will utilise hBSCs as a model to study molecular determinants of breast cancer associated with deregulation of their self-renewal machinery.

The in vitro multi-lineage differentiation potential of breastmilk-derived stem cells together with the lack of tumor formation in recipient animals suggest the potential use of hBSCs as a therapeutic alternative to hESCs and hiPSCs, the use of which is hindered by the ethical and safety issues discussed above (Takahashi et al., 2007; Miura et al., 2009; Ghosh et al., 2011). Because of its ethical, non-invasive and plentiful nature, breastmilk offers a novel resource of patient-specific stem cells for applications in regenerative medicine.

In light of the above, it will be appreciated that in accordance with the present invention, BSCs can be isolated, expanded and enriched. Conveniently, the BSCs may be expanded as spheroids. As indicated above, such BSCs or spheroids may be used for autologous cell therapies of the breastmilk donor or of individuals having a matching immunogenicity profile. Advantageously, the BSCs of the present invention may also be used in heterologous, therapeutical applications.

It will further be appreciated that the cell therapy can consist of therapy comprising administering the pluripotent cells or the spheroids comprising or consisting of the BSCs of the invention or of administering more committed/differentiated cells which are directly derived from the BSCs or from the spheroids comprising or consisting of the BSCs.

Furthermore, the skilled addressee will understand that compositions comprising the BSCs or the spheroids comprising or consisting of the BSCs of the present invention or more committed/differentiated cells directly derived from the BSCs or the spheroids comprising or consisting of the BSCs of the invention may be prepared. Such compositions may be formulated to allow storage or transport of viable cells—either in the form of individual BSCs or in the form of spheroids comprising or consisting of the BSCs. Alternatively, the compositions may be pharmaceutical compositions for therapeutical administration comprising the BSCs or the spheroids comprising or consisting of the BSCs of the present invention or more committed/differentiated cells directly derived from the BSCs or the spheroids comprising or consisting of the BSCs of the invention.

As indicated above, in a further embodiment, the present invention relates to methods of expanding the BSC population such that large cell numbers can be obtained either as individual cells or as a plurality of spheroids comprising or consisting of the BSCs. These cells or spheroids can then be banked in cell banks such that they can be made available at a later stage. With a clear trend towards personalised medicine, banked cells according to the present invention provide a valuable source of therapeutic cells.

In light of the above, it will also be appreciated that breastmilk and the BSCs or the spheroids comprising or consisting of the BSCs of the present invention can serve as a valuable resource for breast cancer research. Specifically, it is proposed that cells of different degrees of differentiation of the mammary gland may serve as model systems for aberrant cell growth and proliferation in breast cancer. As such, the BSCs or the spheroids comprising or consisting of the BSCs of the present invention can provide new cell culture model systems for breast cancer research.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention.

What is claimed is:

1. A method of preparing breastmilk stem cell(s) (BSC) or a spheroid comprising BSC, comprising the steps of:
    a) separating cells from non-cellular portions of breastmilk obtained from a subject, wherein said cells comprise a mixture of cells;
    b) growing the mixture of cells in suspension culture to form one or more spheroid; and
    c) harvesting said one or more spheroids, wherein said one or more spheroids comprise said BSC.

2. The method of claim 1 wherein the step of growing said mixture of cells comprises the proliferation of a cell.

3. The method of claim 1 or claim 2 wherein the step of growing said mixture of cells comprises selective proliferation of said BSC.

4. The method of claim 1 wherein said at least one spheroid is harvested after growing in suspension culture for up to 12-14 days.

5. The method of claim 1 wherein said at least one spheroid is harvested after growing in suspension culture for 9 days.

6. The method of claim 1, further comprising the step of passaging said at least one spheroid in suspension culture after step (b) and before step (c).

7. The method of claim 6 wherein said passaging comprises dissociating said at least one spheroid.

8. The method of claim 1 wherein said at least one spheroid is grown in a low-binding cell culture vessel.

9. The method of claim 1 wherein said at least one spheroid is grown in a feeder-free culture.

10. The method of claim 1 wherein the step of growing said mixture of cells in suspension culture comprises growing said cells in the presence of any one or more of the following, or combinations thereof: growth factors, insulin, transferrin, selenium, nicotinamide, dexamethasone, fetal bovine serum or non-essential amino acids (NNEA).

11. The method of claim 10, wherein said growth factors are selected from epidermal growth factor and fibroblast growth factor.

12. The method of claim 1 wherein said BSC is a pluripotent stem cell.

13. The method of claim 1 wherein the breastmilk is human breastmilk and wherein said BSC is a human pluripotent stem cell.

14. The method of claim 13 wherein said human BSC (hBSC) expresses Oct4, Sox2, Nanog and/or Klf4.

15. The method of claim 13 wherein said human BSC (hBSC) expresses Oct4, Sox2, Nanog, SSEA4 and TRA-1-60/81.

16. The method of claim 1 wherein said breastmilk is obtained from a subject after initiation of feeding.

17. The method of claim 16 wherein said breastmilk is collected after or at the end of said feeding.

18. The method of claim 17 wherein said breastmilk is collected from about 0 minutes to about one hour after said feeding.

19. The method of claim 17 or claim 18 wherein the breastmilk is collected about 25-30 minutes after said feeding.

20. The method of claim 1 further comprising the step of differentiating said BSC.

21. The method of claim 20 wherein said BSC is differentiated to become a myoepithelial cell, a luminal cell, a lactocyte, a neural cell, a stromal cell, an osteoblast, a chondrocyte, an adipocyte, a cardiomyocyte, a hepatocyte, or a beta islet cell.

* * * * *